(12) United States Patent
Breakspear et al.

(10) Patent No.: US 10,646,129 B2
(45) Date of Patent: May 12, 2020

(54) BURST ANALYSIS

(71) Applicant: The Council of the Queensland Institute of Medical Research, Herston, Queensland (AU)

(72) Inventors: Michael Breakspear, Herston (AU); James Roberts, Herston (AU); Sampsa Vanhatalo, Helsinki (FI)

(73) Assignee: THE COUNCIL OF THE QUEENSLAND INSTITUTE OF MEDICAL RESEARCH, Herston, Queensland (AU)

( * ) Notice: Subject to any disclaimer, the term of this patent is extended or adjusted under 35 U.S.C. 154(b) by 449 days.

(21) Appl. No.: 15/038,363

(22) PCT Filed: Nov. 20, 2014

(86) PCT No.: PCT/AU2014/050364
§ 371 (c)(1),
(2) Date: May 20, 2016

(87) PCT Pub. No.: WO2015/074116
PCT Pub. Date: May 28, 2015

(65) Prior Publication Data
US 2016/0287117 A1    Oct. 6, 2016

(30) Foreign Application Priority Data
Nov. 20, 2013    (AU) .................................. 2013904486

(51) Int. Cl.
*A61B 5/04* (2006.01)
*A61B 5/0476* (2006.01)
(Continued)

(52) U.S. Cl.
CPC ...... *A61B 5/04012* (2013.01); *A61B 5/04017* (2013.01); *A61B 5/0476* (2013.01);
(Continued)

(58) Field of Classification Search
None
See application file for complete search history.

(56) References Cited

U.S. PATENT DOCUMENTS 6,288,001 B1 * 9/2001 Kiyota .................. B22D 41/02
501/100
6,931,274 B2 8/2005 Williams
(Continued)

FOREIGN PATENT DOCUMENTS

WO    2015/074116 A1    5/2015

OTHER PUBLICATIONS

Sinclair et al. (EEG and long-term outcome of term infants with neonatal hypoxicischemic encephalopathy; Clinical Neurophysiology 110 (1999) 655-659).*
(Continued)

*Primary Examiner* — Kaylee R Wilson
*Assistant Examiner* — Jay B Shah
(74) *Attorney, Agent, or Firm* — Schwabe Williamson & Wyatt, PC

(57) ABSTRACT

Methods and an apparatus are provided, which may be used for determining the prognosis and/or diagnosis of a subject demonstrating burst suppression, whereby the subject has or is at risk of developing brain damage. In particular, the methods and apparatus determine the prognosis and/or diagnosis through the detection of bursts from a reading of electrical and/or electromagnetic activity of the subject's brain, such as an electroencephalogram (EEG), and subsequent analysis of one or more burst metrics derived therefrom.

11 Claims, 14 Drawing Sheets

(51) Int. Cl.
*A61B 5/00* (2006.01)
*G16H 50/20* (2018.01)
*G16H 50/30* (2018.01)
*A61B 5/145* (2006.01)

(52) U.S. Cl.
CPC .......... *A61B 5/4064* (2013.01); *A61B 5/7264* (2013.01); *A61B 5/7275* (2013.01); *G16H 50/20* (2018.01); *G16H 50/30* (2018.01); *A61B 5/14542* (2013.01); *A61B 5/6814* (2013.01); *A61B 2503/045* (2013.01)

(56) References Cited

U.S. PATENT DOCUMENTS

| | | | | |
|---|---|---|---|---|
| 2004/0220489 | A1* | 11/2004 | Sherman | A61B 5/046 600/518 |
| 2005/0245973 | A1* | 11/2005 | Sherman | A61B 5/046 607/5 |
| 2010/0114526 | A1* | 5/2010 | Hosking | G06F 17/18 702/181 |

OTHER PUBLICATIONS

Chalak et al. (Low Voltage aEEG as predictor of Intracranial Hemorrhage in preterm infants; Pediatr Neurol. May 2011 ; 44(5): 364-369).*

Iyer et al. Novel features of early burst suppression predict outcome after birth asphyxia, 2014; Annals of Clinical and Translational Neurology 2014; 1(3): 209-214.*

Löfhede; Classification of Burst and Suppression in the Neonatal EEG; Department of Signals and Systems Biomedical Signals and Systems Chalmers University of Technology 2007 (Year: 2007).*

Clauset et al; Power-Law Distributions in Empirical Data; SIAM Review; vol. 51, No. 4, pp. 661-703; 2009 (Year: 2009).*

Kapucu et al.—Burst analysis tool for developing neuronal networks exhibiting highly varying action potential dynamics; Frontiers in Computational Neuroscience; Frontiers in Computational Neuroscience ; 2012 (Year: 2012).*

Lofhede, J. "The EEG of the Neonatal Brain—Classification of Background Activity", PhD Thesis, Chalmers University of Technology, 2009, 187 pages.

Wang, Y. et al., "Automatic Detection of Burst Suppression", Proceedings of the 29th Annual International Conference of the IEEE EMBS, 2007, pp. 553-556.

Meyers, M.M. et al., "Developmental Profiles of Infant EEG: Overlap with Transient Cortical Circuits", Clinical Neurophysiology, 2012, vol. 123 No. 8, pp. 1502-1511.

Lofhede, J. et al., "Automatica Classification of Background EEG Activity in Healthy and Sick Neonates", Journal of Neural Engineering, 2010, vol. 7 No. 1, pp. 1-12 (Abstract only).

Kessler, S.K. et al., "Short-Term Outcome Prediction by Electroencephalographic Features in Children Treated with Therapeutic Hypothermia After Cardiac Arrest", Neurocritical Care, 2011, vol. 14 No. 1, pp. 1-13.

Arnold M et al., "Use of adaptive Hilbert transformation for EEG segmentation and calculation of instantaneous respiration rate in neonates", Journal of Clinical Monitoring, Springer Netherlands, Dordrecht, (Jan. 1, 1996), vol. 12, No. 1; 18 pages.

Vladana Djordjevic et al., "Feature extraction and classification of EEG sleep recordings in newborns", Information Technology and Applications in Biomedicine, 2009. ITAB 2009. 9th International Conference On, Piscataway, NJ, USA, (Nov. 1, 2009); 4 pages.

B. G. Farley et al, "Computer Techniques for the Study of Patterns in the Electroencephalogram", IRE Transactions on Bio-Medical Electronics (Jan. 1, 1962); pp. 4-12.

Matthias Wacker et al., "A processing scheme for time-variant phase analysis in EEG burst activity of premature and full-term newborns in quiet sleep: a methodological study", doi:10.1515/bmt-2012-0034, (Jan. 1, 2012), pp. 491-505.

Sourya Bhattacharyya et al., "Feature Selection for Automatic Burst Detection in Neonatal Electroencephalogram", IEEE Journal on Emerging and Selected Topics in Circuits and Systems, IEEE, Piscataway, NJ, USA, (Dec. 1, 2011), vol. 1, No. 4; pp. 469-479.

Extended European Search Report for EP Application No. 14864081.6 dated Jun. 22, 2017; 13 pages.

Patent Cooperation Treaty: International Preliminary Search Report on Patentability for PCT/AU2014/050364 dated May 24, 2016; 7 pages.

Patent Cooperation Treaty: International Search Report and Written Opinion for PCT/AU2014/050364 dated May 28, 2015; 12 pages.

Cloostermanns, et al. "A novel approach for computer assisted EEG monitoring in the adult ICU" Clinical Neurophysiology, vol. 122:2100-2109 (2011).

* cited by examiner

BURST ANALYSIS

FIELD OF THE INVENTION

The present invention relates to the field of neurophysiology. More particularly, the invention relates to methods and an apparatus for determining a prognosis in a subject at risk of developing brain damage. Further, the invention relates to methods and an apparatus for diagnosing brain damage in a subject at risk of developing such damage.

BACKGROUND TO THE INVENTION

Burst suppression (BS) is an electroencephalogram (EEG) pattern typically characterized by low amplitude or suppressed EEG activity punctuated by segments of irregular high amplitude bursts. The presence of BS in EEG recordings has long been identified as indicating acute compromise of brain functioning (Niedermeyer et al., Clin EEG, 1999). Additionally, BS is also observed during the deep stages of general anaesthesia and in conjunction with sedative overdoses, the so-called benign neuropharmacologically-induced BS.

Asphyxia may result in severe brain damage and/or deficits and if so is associated with a poor outcome. Scalp EEG is routinely used to monitor the brain's electrical activity in asphyxic patients and clinicians often assess EEGs in an attempt to reliably and rapidly distinguish between such patients who will benefit from therapeutic intervention, and/or those with a poorer prognosis who may not recover or recover with severe neurological damage and/or deficits.

Following an initial period of quiescence, the EEG from an asphyxic patient typically exhibits BS across most cortical regions of the brain (Niedermeyer et al., Clin EEG, 1999). Individual bursts vary greatly in magnitude and shape, ranging from very brief fluctuations that barely surpass amplifier and physiological noise to high-amplitude waveforms that can last for several seconds. Complete neurological recovery typically occurs only in cases where BS rapidly resolves and normal, continuous EEG activity resumes.

Therefore, a successful clinical outcome depends crucially on the rapid cessation of bursting and the resumption of continuous cortical activity in patients with asphyxia. Despite its importance in the recovery process, mechanisms of BS remain poorly understood, and objective diagnostics are needed to guide clinical decision making including treatment.

By way of example, identification of BS and its recovery time in asphyxic newborns is commonly used as a prognostic indicator of clinical outcome, which may be used to guide clinicians as to who may benefit from maximal care. The interpretation of BS in asphyxic newborns, however, typically only recognizes its presence versus its absence. While a qualitative assessment of "burst sparseness"—a low overall frequency of bursts—may be taken as an additional sign of severity (Walsh, Clin Neurophysiol, 2011), no properties of the bursts themselves have been shown to be useful prognostic indicators. Moreover, while clinical decisions to commence therapeutic hypothermia after birth asphyxia are often based on observing BS in the early EEG, hypothermia treatment itself can significantly delay BS recovery, hence compromising the utility of an early EEG in outcome prediction (Hallberg et al., Acta Paediatrica, 2010).

Bursting activity patterns such as BS represent a pathologically abnormal EEG pattern in neonates. These types of abnormal patterns extend to preterm neonates in which busting patterns also reflect immature cortical development. The transition from BS to discontinuous EEG patterns is also commonly observed. Discontinuous activity patterns have increased levels of bursting compared with BS yet are still classified as abnormal background patterns. In essence, EEG bursting patterns in the neonate stem from a triumvirate of BS, discontinuous (periodically alternating bursts and interbursts) and continuous activity patterns.

Additionally, early brain development depends upon spontaneously occurring, intermittent electrical activity that supports neuronal survival and sustains primary growth of brain networks. These bursting periods vary in their temporal evolution and spatial synchronicity across the cortex and are typically observed in preterm ages of 24-30 weeks. In the latter half of pregnancy, this electrical activity is highly sensitive to various endogenous and exogenous disturbances, creating clinical challenges in the acute care of preterm newborn infants. Despite advances in neonatal intensive care units (NICUs) worldwide, early preterm birth is still associated with a high risk of neurological morbidity (Back and Miller 2014). A major endeavor in NICUs worldwide is to complement early cardiorespiratory support with intensive brain monitoring, so as to identify early indices of cortical disturbance and guide appropriate clinical interventions.

Currently, preterm brain monitoring primarily involves visual assessment of electroencephalography (EEG) amplitudes (a.k.a. amplitude integrated EEG, aEEG; Hellstrom-Westas and Rosen, 2004; Olischar et al, 2004; Wikstrom et al, 2012) and the variation in EEG waveforms. These approaches toward EEG assessment in preterm infants, however, suffer from being qualitative, relying upon subjective appraisal, and being vulnerable to confounding factors arising from technical artefacts. Hence, there is an unmet need to derive cortical activity signatures of early brain function in preterm infants that are robust, objective, and based on firm statistical evidence.

SUMMARY OF THE INVENTION

In a first aspect, the invention resides in a method of detecting a plurality of bursts in a reading of electrical and/or electromagnetic activity from a subject's brain including the steps of:
(i) compute an instantaneous amplitude for the reading of electrical and/or electromagnetic activity over time, and
(ii) apply a threshold level of instantaneous amplitude that detects a plurality of bursts in said reading, wherein a maximum instantaneous amplitude of the plurality of detected bursts is greater than or equal to said threshold level.

Preferably, the threshold level detects an approximately maximum number of bursts in the reading from said subject.

In one embodiment, the threshold level of instantaneous amplitude is that which detects at least 95% of bursts in said reading from the subject.

Suitably, the instantaneous amplitude for said reading is computed by Hilbert transform.

In one particular embodiment, the method of this aspect further includes the step of squaring the instantaneous amplitude computed in (i) prior to applying the threshold level in (ii).

In a second aspect, the invention resides in a method of determining a diagnosis and/or prognosis of a subject with brain damage and/or at risk of developing brain damage including the steps of:

(i) acquire a reading of electrical and/or electromagnetic activity from the brain of the subject over time;
(ii) detect a plurality of bursts in said reading;
(iii) compute one or more burst metrics from said bursts wherein the one or more burst metrics are selected from the group consisting of: a burst area metric, a relationship between burst duration and burst area metric and a burst shape metric;
(iv) submit one or more burst metrics to a classifier that determines the prognosis and/or diagnosis of said subject according to said metrics.

Suitably, the subject has asphyxia or is at risk of developing asphyxia.

The subject is preferably a human. In certain embodiments, the subject is a newborn infant born full term, postterm or preterm. In one particular embodiment, the newborn infant is suffering from hypoxic ischemic encephalopathy. In one embodiment, the subject is receiving or undergoing hypothermia therapy.

Suitably, the step of detecting bursts uses a thresholding method. Preferably, this method is an adaptive thresholding method calculated for each individual patient. The thresholding method may further utilise one or more initial pre-processing functions, such as the Hilbert transform and/or squaring the amplitude of the electrical and/or electromagnetic signal. In a preferred embodiment, bursts are detected according to the method of the first aspect.

The step of computing one or more burst metrics suitably utilises the measures of burst shape, burst duration, burst area (or burst size) and the relationship between burst duration and burst area from the plurality of bursts detected. The burst area metric is suitably the scaling exponent ($\alpha$) of the cumulative distribution function of all burst areas calculated. The relationship between burst duration and burst area metric is suitably the slope of the linear relationship between burst area and burst duration of individual bursts plotted in a double logarithmic fashion (log-log scale). The burst shape metric is suitably selected from the group consisting of burst skewness and burst kurtosis.

Suitably, one or more of the burst metrics described above are submitted to the classifier. In particular embodiments, the classifier compares the one or more burst metrics to one or more threshold metric levels, such that an altered or modulated burst metric relative to the one or more threshold metric levels indicates or correlates with an increased or decreased probability of the subject having brain damage and/or having a poor prognosis. In one preferred embodiment, the classifier comprises a database configured to compare the one or more burst metrics to the one or more threshold metric levels. Suitably, the one or more threshold metric levels are or comprise a control or reference population level. Preferably, more than one burst metric is submitted prior to determining a prognosis and/or diagnosis. In one embodiment, the one or more threshold metric levels are configured to determine the subject has or is at risk of developing intraventricular haemorrhage.

In a third aspect, the invention resides in an apparatus for determining a risk of developing brain damage and/or detecting brain damage in a subject comprising:
(i) a detector for detecting a plurality of bursts from a reading of electrical and/or electromagnetic activity from the subject's brain;
(ii) a processor for computing one or more burst metrics from the plurality of bursts, wherein the burst metrics are selected from the group consisting of: a burst area metric, a relationship between burst duration and burst area metric and a burst shape metric; and
(iii) a classifier that determines the risk of developing brain damage and/or detects brain damage in the subject by analysis of the one or more burst metrics.

In one embodiment, the apparatus further comprises a device for recording the reading of electrical and/or electromagnetic activity from the subject's brain.

Suitably, the apparatus is for use in the method of the first and/or second aspects.

With regard to the aforementioned aspects, the reading of electrical activity from the brain of a subject is suitably an EEG.

Further features and advantages of the present invention will become apparent from the following detailed description.

BRIEF DESCRIPTION OF THE DRAWINGS

To assist in understanding the invention and to enable a person skilled in the art to put the invention into practice, preferred embodiments of the invention will be described by way of example only with reference to the accompanying drawings, in which.

DETAILED DESCRIPTION OF THE INVENTION

Throughout this specification, unless the context requires otherwise, words such as "includes" or "comprises" will be understood to imply the inclusion of a stated integer or group of integers but not the exclusion of any other integer or group of integers.

As used in this specification the indefinite articles "a" and "an" may refer to one entity or a plurality of entities (e.g. proteins) and are not to be read or understood as being limited to a single entity.

As would be readily understood by the skilled artisan, "burst suppression" or BS describes the pattern of electrical activity on an EEG typically characterised by alternating stretches of "bursts" and relatively suppressed or reduced EEG activity. An example of burst suppression can be observed in FIG. 5A. As used herein, "bursts" refers to those periods of elevated electrical activity between the intervening periods of relative quiescence on an EEG.

There are typically two broad types of BS. Firstly, there is that evident in the brain of an asphyxic subject suffering from, for example, those conditions or disorders described hereinafter. The second type is benign, neuropharmacologically-induced BS, such as that observed in the deep stages of general anaesthesia or in conjunction with sedative overdoses. Much of the description makes reference to BS in asphyxic subjects, but the invention should not be understood to be limited to this particular subject group. Indeed, alternating bursting patterns similar to burst suppression is described herein to be present in preterm infants of a gestational age of approximately 22 to 28 weeks.

Figure 1:
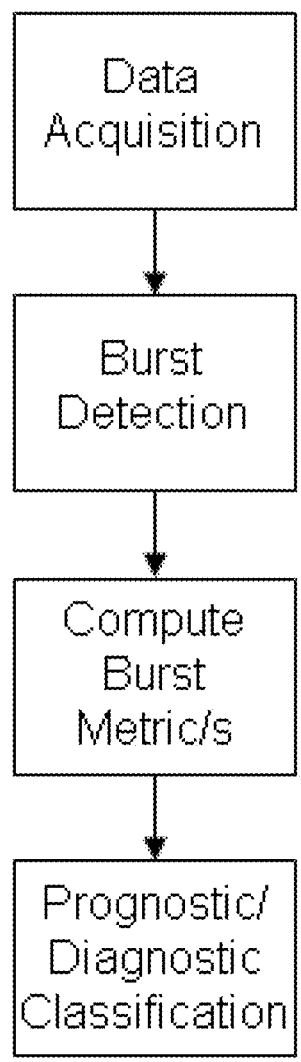
FIG. 1 is a flowchart showing the major steps of a method of determining a prognosis and/or diagnosis in a subject.

Referring to FIG. 1 there is provided a flowchart that outlines a method of determining a prognosis and/or diagnosis for a subject demonstrating burst suppression. Broadly, the method of the present invention commences with recording the electrical and/or electromagnetic activity of the subject's brain typically by using an EEG. This data is acquired over time such that a plurality of bursts can be detected and subsequently analysed. To this end, one or more prognostic/diagnostic burst metrics are computed from the burst measures of burst duration, burst area (or burst size) and burst shape for each burst in a recording. Once computed, one or more burst metrics are then classified to provide a prognosis as to the clinical outcome, and in particular the risk of subsequently developing brain damage, and/or a diagnosis of brain damage for the respective subject.

By "determining a prognosis" meant the prediction of the course or outcome of a condition in a patient. This prediction need not be 100% accurate, nor that a given course or outcome is more or less likely to occur than not. Rather, the person skilled in the art would understand that the term "prognosis" refers to an increased or decreased probability that a certain course or outcome will occur in a subject exhibiting a given characteristic, such as the presence or level of a prognostic indicator or metric, when compared to those subjects not exhibiting the characteristic.

By way of example, and as described hereinafter, a subject exhibiting an elevated or reduced prognostic burst metric may be more likely to suffer from an adverse neurodevelopmental and/or physical developmental outcome than subjects respectively exhibiting a reduced or elevated prognostic burst metric. Additionally, determining a prognosis may also facilitate predicting the overall probability of survival of a subject. For example, an elevated prognostic burst metric in a subject may suggest reduced survival prospects than those subjects with a low prognostic burst metric.

By "brain damage" is meant the destruction, degeneration, deterioration and/or impaired development and/or growth of brain cells and/or tissue. Such damage may be focal or localised, such as may occur in stroke. Alternatively, the brain damage may be diffuse or global thereby involving several or all areas of the brain. The skilled artisan would readily appreciate that the severity of the brain damage resulting from asphyxia can vary greatly. Furthermore, the brain damage need not be permanent, particularly if the damage is mild.

By "asphyxia" or "asphyxic" is meant a condition in which there is a significant decrease in the concentration of oxygen in the body, which may also be accompanied by an increased carbon dioxide concentration, which may lead to unconsciousness and ultimately death. Included within the scope of this term are anoxia, which is characterised by an absence or complete lack of oxygen supply to the body or part thereof, hypoxia, which refers to a lower than physiological normal supply of oxygen to the body or part thereof, and ischemia, which is characterised by an insufficient or complete lack of blood supply to the body or part thereof.

Accordingly, in asphyxia the brain is typically deprived of freshly oxygenated blood. Without a steady supply of freshly oxygenated blood, the brain may cease to function and after resuscitation, if successful, a proportion of patients may suffer some damage to the brain and/or associated neurologic tissues. Without limitation thereto, this situation may arise as a result of, for example, cardiac arrest, respiratory arrest, stroke and other cerebrovascular trauma, suffocation, drowning, strangulation, electrocution, toxic poisoning, metabolic insults or other similar trauma.

Suitably, the method of the invention is performed on a newborn infant. The term "newborn" or "newborn infant" as used herein is intended to describe infants (i.e., infant humans) typically being less than one month old, preferably less than one week old and even more preferably less than one day old. The term is meant to include preterm (less than 37 weeks gestation), full term (37 to 42 weeks gestation) and postterm infants (greater than 42 weeks gestation).

In one embodiment, the method is performed on a newborn infant suffering from hypoxic ischemic encephalopathy (HIE). It would be understood, that HIE results in damage to cells of the central nervous system (i.e., the brain and spinal cord) from inadequate oxygen supply to these tissues. HE may cause death in the newborn period or result in neurodevelopmental delay, mental retardation, and/or cerebral palsy. While HIE is typically associated with oxygen deprivation in newborns due to birth asphyxia, it can occur in all age groups, such as a complication of cardiac arrest.

In a further embodiment, the diagnostic and/or prognostic methods are performed on a preterm newborn infant demonstrating burst suppression. Suitably, the preterm infant is of gestational age of approximately 22 to 28 weeks.

It would be appreciated that the method may be performed only once on a subject over a period of time or alternatively it may be performed at multiple time points in a subject. In certain embodiments, the method of the present invention is performed on a reading of electrical and/or electromagnetic brain activity taken from a subject within 12, 24, 48 and/or 72 hours of an asphyxic event or the onset of asphyxia in said subject. In further embodiments, the method of the present invention is performed on a reading of electrical and/or electromagnetic brain activity taken from a newborn infant within 12, 24, 48 and/or 72 hours of the birth of said infant, wherein the infant may or may not be suffering from asphyxia.

In broad terms the diagnostic/prognostic method commences with recording the electrical and/or electromagnetic activity of the brain using, for example, an EEG, an electrocorticogram (ECoG; also known as an intracranial EEG)

and/or a magnetoencephalogram (MEG). The data is typically acquired continuously over a period of time such that a sufficient number of bursts may be analysed. For the purpose of description, reference is made to a range of 30 to 600 minutes, but recordings may be shorter, such as 10 minutes, or longer, such as 1000 minutes.

Additionally, the recording from which data is derived may not be contiguous. Indeed, a particular technical advantage of the methods described herein is that they are based on analysing extracted events (bursts). Hence they do not require fully continuous streams of EEG signal. This allows rejection of signal epochs with clear artefacts or the like without loss of analytical reliability, which commonly challenges paradigms relying on continuous temporal behaviour, such as vigilance state cyclicity (Stevenson et al., 2014) or broad spectrum power spectra (Fransson et al., 2013). Accordingly, segments of an EEG recording or the like to be analysed may be precluded from analysis owing to, for example, the presence of excessive artefact or noise.

Extracting clinically-useful information from statistical properties of a very large number of bursts makes the measure largely insensitive to common noise-related confounders that may be present in the electrically-noisy intensive care unit (ICU) or neonatal ICU environment and challenge traditional analyses of EEG monitoring. Moreover, the method of the invention is data-driven, which makes it robust against inter-individual variability in the overall level of EEG amplitudes caused by technical variations (e.g., inter-electrode distance, constant artefact, or subcutaneous swelling).

Figure 2:
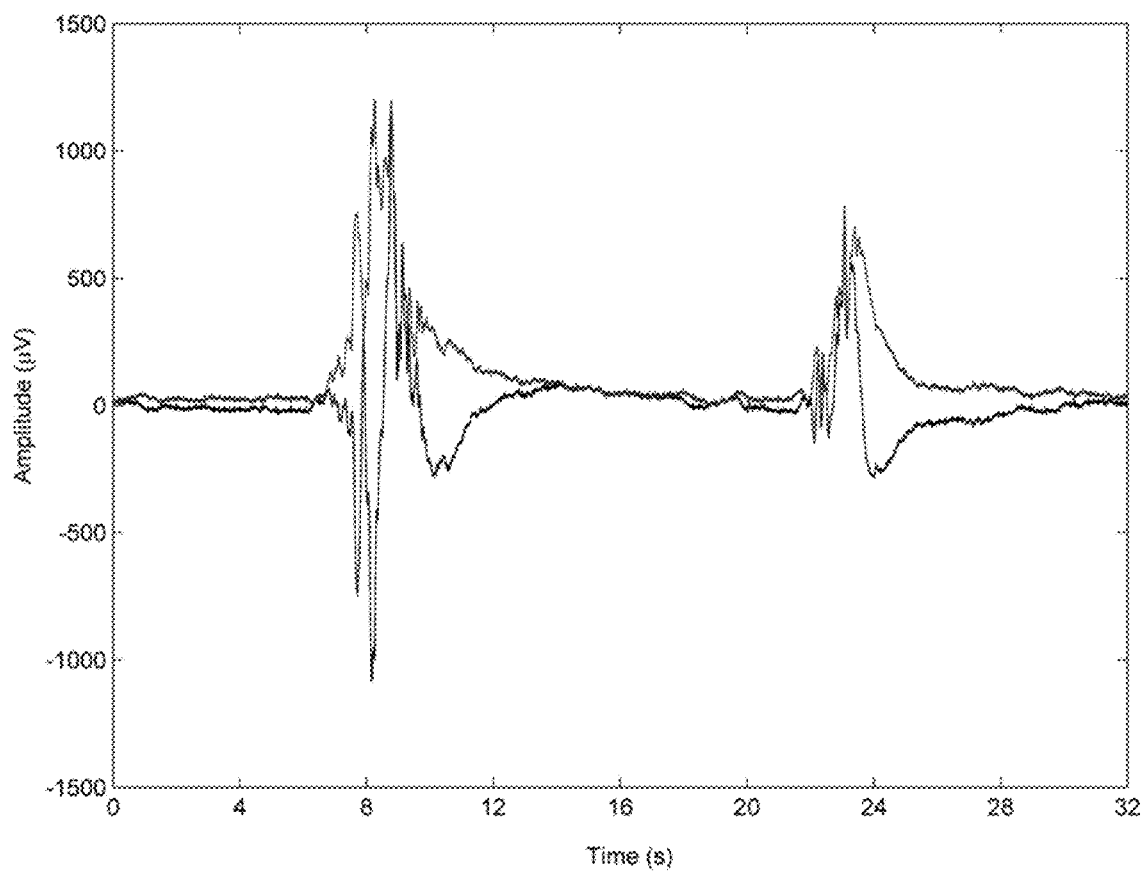
FIG. 2 provides an example EEG demonstrating how the instantaneous EEG amplitude (red; amplitude at each time point) is calculated using the Hilbert transform.

The electrical and/or electromagnetic recordings of brain activity may be pre-processed prior to the identification of bursts. In this regard, the instantaneous amplitude of the EEG may be calculated for the amplitude of the EEG at each time point, whether of a positive or negative value. By way of example, instantaneous amplitude may be calculated by Hilbert transform (FIG. 2). The instantaneous amplitude of the Hilbert or similarly transformed EEG signal may further be processed by the squaring of the EEG amplitude (FIG. 5B) (i.e. the instantaneous power or energy).

As the person skilled in the relevant art would readily acknowledge, the electrical and/or electromagnetic recordings may be pre-processed by a different means, such as NLEO or NLEO-based algorithms, spectrogram-based filtering, artefact rejection, mean root-mean-square and other empirically-derived methods, or even in conjunction with additional means such as mathematical filtering and/or smoothing. In the examples provided, the EEG data underwent smoothing via Savitzy-Golay low pass filtering, followed by calculation of the Hilbert transform by MATLAB software.

Prior to extracting one or more prognostic and/or diagnostic metrics from the bursts, a method is first employed to separate bursts in the EEG recording from any background artefact or noise. In this regard, variance in amplitude arising from background artefacts or noise is a common and a serious confounder of many existing approaches, such as the amplitude-integrated EEG (aEEG, a.k.a. CFM) (Hellström-Westas et al., An Atlas of Amplitude-Integrated EEGs in the Newborn, 2003).

Figure 3:
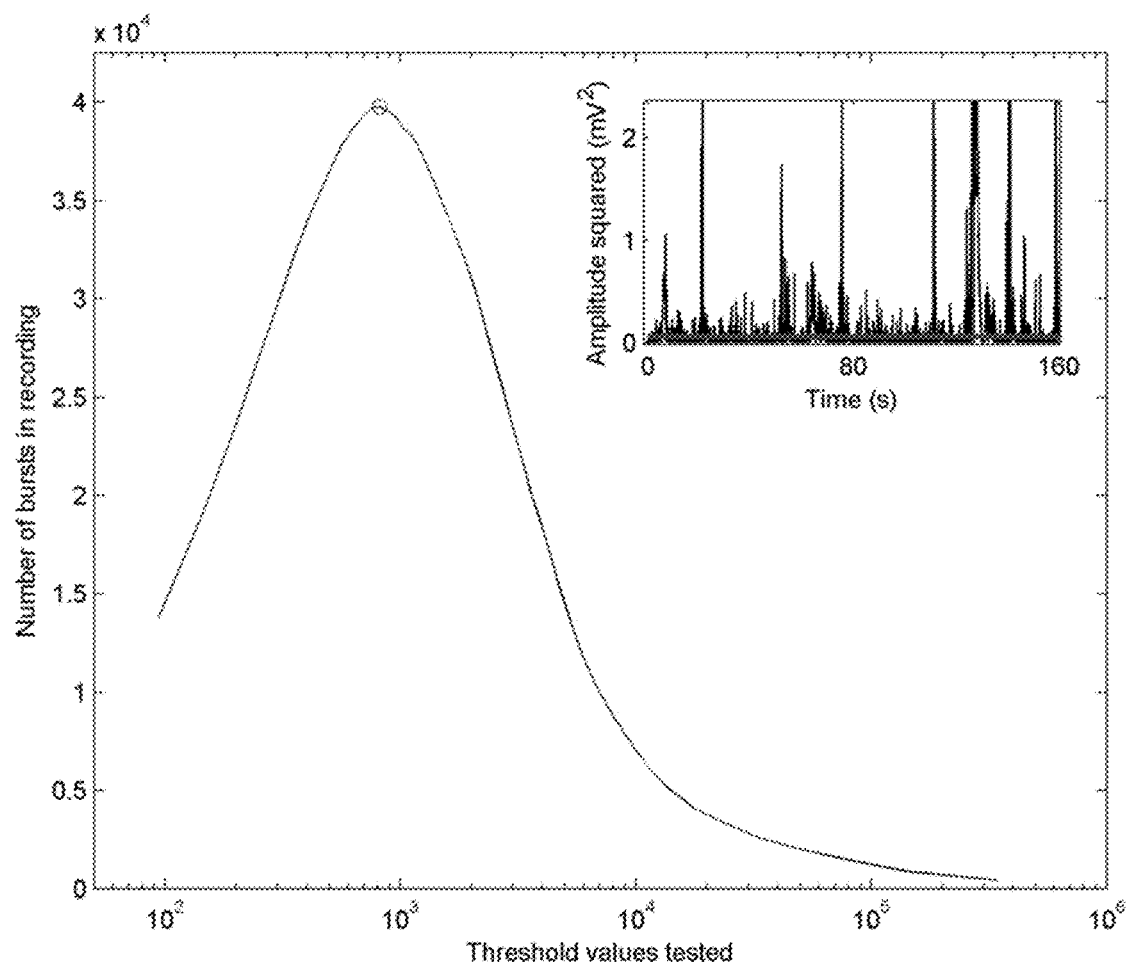
FIG. 3 demonstrates the adaptive thresholding method used to detect bursts and remove background noise or artefact from an EEG reading.
Figure 4:
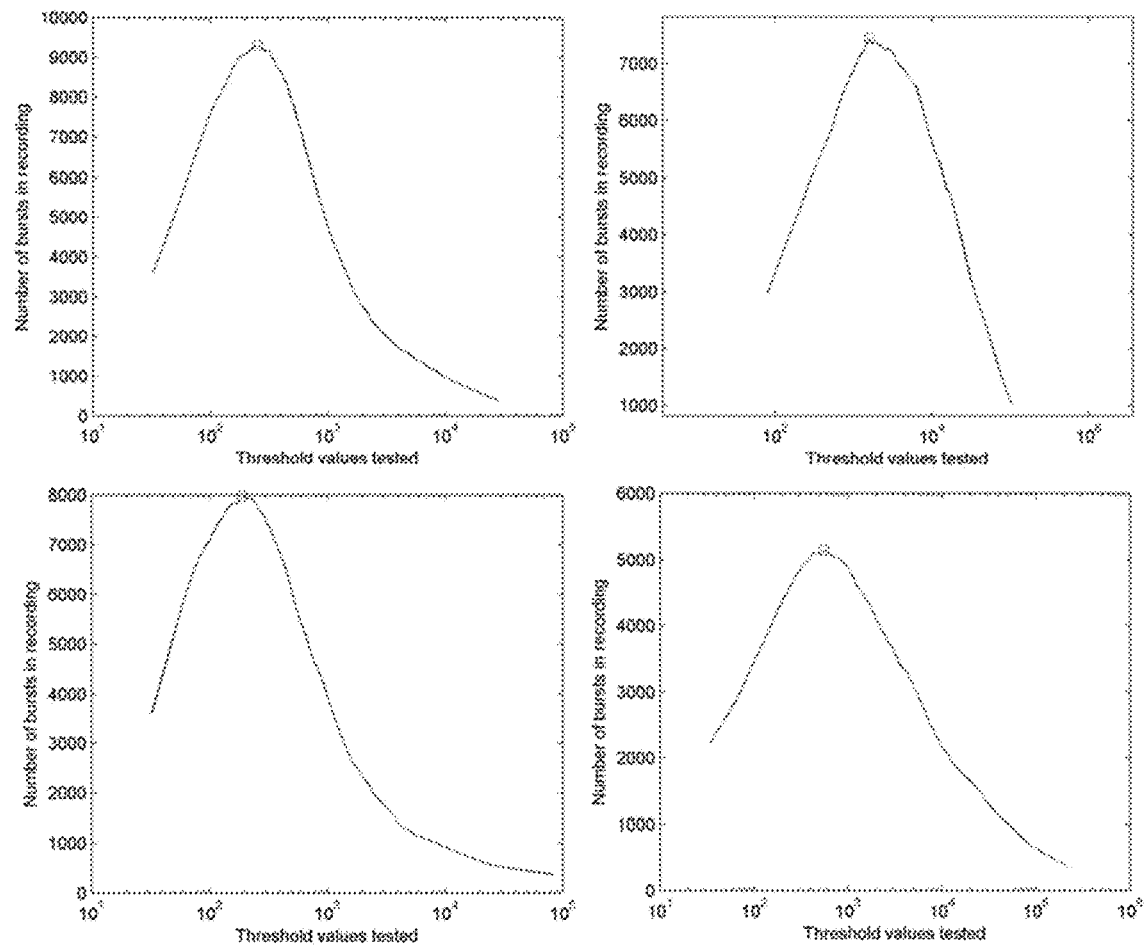
FIG. 4 demonstrates four additional examples of the automated adaptive thresholding method in infant EEG recordings.

To maximise the objectivity of an analysis, a burst detection method that employs automatically and individually defined thresholds is preferably employed. From the example herein, this procedure may involve scanning a wide range of thresholds (shown in the X axis) and quantifying the number of burst detections for each threshold, as illustrated by FIGS. 3 and 4. Very low thresholds—such as below the noise level—yield very few bursts. As the threshold rises above the noise floor, supra-threshold bursts emerge although for small thresholds many of these will be artificially merged. Very high thresholds fail to detect small bursts and, in the extreme, fail to detect any bursts at all.

Suitably, a burst is detected if its maximum instantaneous amplitude is greater than or equal to that of an applied threshold level. Since the instantaneous amplitude may not only be positive but also negative, this may mean that a burst is detected if its maximum instantaneous amplitude is more negative than that of the applied threshold level.

Preferably, the threshold level of burst amplitude, and in particular instantaneous amplitude, as unique to each subject, is the one that produces the most burst detections (i.e. detects a maximum or approximately maximum amount of bursts) as indicated by the red circles in FIGS. 3 and 4. This adaptive thresholding method overcomes the known ambiguity associated with visual burst detection (Palmu et al., Clin Neurophysiol, 2010). The invention, however, is not to be limited to the specific thresholding method described herein or any other such method. In fact, the burst metrics described herein are reliable prognostic indicators when calculated over a broad range of threshold levels.

The skilled artisan would readily understand that the threshold level of burst amplitude used to detect bursts is likely to differ between individuals (for example see FIG. 4) owing, at least in part, to technical differences in the measurement of EEG recordings and the like, such as EEG machine variability and inter-electrode distance and placement. As can be seen in FIG. 4, however, the relationship between thresholds and the number of bursts follows the same unimodal distribution with one threshold value per individual yielding the highest number of burst detections (i.e., the adaptive threshold). In this regard, however, detecting a maximum number of bursts from the EEG recording or the like from a subject may not necessarily detect 100% of the individual bursts therefrom.

In particular embodiments of the present invention, the threshold level of burst amplitude, and in particular instantaneous amplitude, detects or identifies less than 100% of the individual bursts from the subject's EEG reading or the like. In some embodiments, the threshold level of burst amplitude, and in particular instantaneous amplitude, detects or identifies at least 20%, 25%, 30%, 35%, 40%, 45%, 50%, 55%, 60%, 65%, 70%, 75%, 80%, 85%, 90% or 95% of the individual bursts from the subject's EEG reading or the like. Preferably, the threshold level of burst amplitude, and in particular instantaneous amplitude, detects or identifies at least 95% of the individual bursts from the subject's EEG reading or the like.

Figure 5:
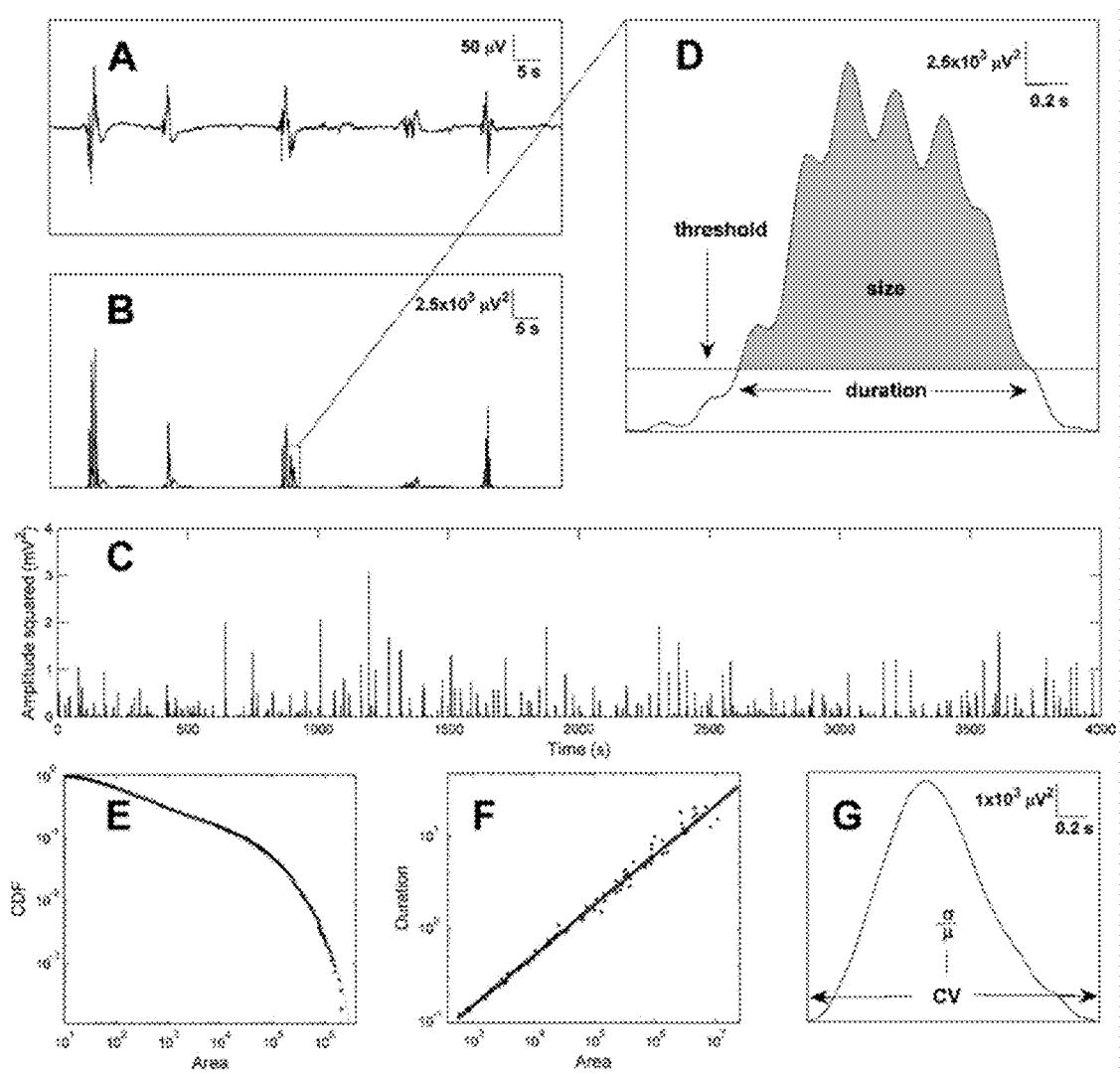
FIG. 5 demonstrates an EEG reading with burst suppression and its transformation to derive burst metrics.

Once a plurality of bursts are detected from the EEG reading or the like, the BD (time between successive threshold crossings) and/or BA (i.e., burst size, supra-threshold area under the curve) may be calculated for each burst as illustrated in FIG. 5D. From these measures of BD and/or BA the prognostic burst metrics of (i) the burst area metric, and/or (ii) the relationship between burst area and burst duration metric may then be calculated.

In one embodiment, the burst area metric is the scaling exponent ($\alpha$) of the cumulative distribution function (i.e., $P(X>x)$) of all burst areas calculated. The scaling exponent (the slope of the linear relationship in log-log coordinates) may be calculated using a linear, least-squares fit method. As would be understood by the skilled artisan, the scaling exponent may also be calculated by fitting the distribution to the data using a maximum-likelihood estimator.

In one embodiment, the relationship between burst area and burst duration metric is the slope of the linear relationship between burst area and burst duration of individual bursts plotted in a double logarithmic fashion (i.e., a log-log scale), as evidenced by FIG. 5F.

Additionally or optionally, a burst shape metric of the plurality of detected bursts may be quantified. In one embodiment, the burst shape metric is selected from the group consisting of burst skewness and burst kurtosis.

As referred to herein, "burst skewness" describes asymmetry of a burst from a normal shape or distribution. An increase in "burst skewness" can come in the form of negative skewness or positive skewness, depending on whether data points are skewed to the left (positive skew) or to the right (negative skew) of the data average. For example, leftward or positive skew may be observed in FIG. 14 in pre-IVH and IVH neonates.

In one embodiment, an increase in burst skewness indicates a positive skew or leftward asymmetry of the subject's bursts. In an alternative embodiment, an increase in burst skewness indicates a negative skew or rightward asymmetry of the subjects bursts The term "burst kurtosis" as used with respect to the present invention is a measure of the "peakedness" or "sharpness" of the subjects bursts relative to a normal shape or distribution. Accordingly, an increase in "burst kurtosis" refers to an increase in the "peakedness" or "sharpness" of a subject's bursts, as observed in FIG. 14 in pre-IVH and IVH neonates.

It would be understood that not all bursts within, for example, an EEG recording may demonstrate altered or modulated sharpness (i.e., burst kurtosis) and/or asymmetry (i.e., burst skewness). Indeed, alterations in burst skewness and/or kurtosis may only be evident in bursts of particular duration or time-scale, such as observed in FIGS. 15A and B. Suitably, the burst shape metric is quantified across one or more ranges or timescales of burst duration, such as from 0.1 ms up to 6 s in length. By way of example, such ranges or timescales of burst duration may include 0.1-200 ms, 200-600 ms, 600-1000 ms, 1-2 s, 2-2.75 s, 2.75-3.5 s, 3.5-4.25 s and greater than 4.25 s. As would be appreciated by the skilled artisan, additional ranges of burst duration for quantifying a burst shape metric are contemplated by the invention. In a particular embodiment, a burst shape metric is calculated for detected bursts having a duration of 1 s or greater. In a further embodiment, a burst shape metric is calculated for detected bursts having a duration of 2 s or greater.

Following computation, the burst metric/s may then be classified into a number of categories and/or levels, such as high or low. In one embodiment, the classifier includes a database that is configured to compare the one or more prognostic/diagnostic burst metrics to one or more threshold metric levels. In this regard, the database may contain data that may be text based or may include audio, video, or other types of data which may be classified, tagged, searched, or otherwise manipulated or utilised by the classifier in order to, at least in part, determine a prognosis and/or diagnosis of a subject. Indeed, the database may be updated to reflect data that is particular, for example, to a specific patient population or a specific type of recording device, which may correspondingly improve the accuracy of a determined prognosis and/or diagnosis. It would be appreciated that the classifier may utilise information received from an external source, such as a remote database. Similarly, the database may be updated using received data or information from the classifier to improve the accuracy of a prognosis and/or diagnosis for a subject. In particular embodiments, the threshold metric levels of the database are configured to determine the subject has or is at risk of developing a specific type of brain damage, such as intraventricular haemorrhage.

Once categorized, the burst metric may then be used in diagnosing brain damage in a subject and/or determining a prognosis of a subject as to the future development of neurological damage and/or deficits in that subject, and/or for neonatal or young subjects, a prognosis for their neurodevelopmental outcome or early death. Alternatively, the burst metric/s may be compared to a threshold metric level, which when the diagnostic/prognostic metric is altered or modulated (i.e., exceeds or is below this threshold), the subject may be said to (i) have brain damage; and/or (ii) have a higher probability of developing subsequent neurological damage and/or deficits, and additionally, if a neonatal/young subject, a poorer neurodevelopmental outcome or early death. The invention, however, is not limited to this or any particular method of characterising or categorising a subject's burst metric/s.

In particular embodiments, the subject is receiving or undergoing hypothermia therapy. In this regard, studies have shown that the use of hypothermia therapy to lower the body temperature by generally 3° C. to 5° C. not only reduces the risk of death but also the possibility of long-term disability in, for example, infants who survive birth asphyxia. This is presumably by slowing down the formation of free radicals and preventing apoptosis and necrosis in neurons. Methods of hypothermia therapy typically involve either head cooling only, with a special cap with circulating cold water placed on the head of the neonate, or by systemic whole-body cooling with either a thermostatically controlled cooling blanket or hot/cold gel packs placed under or around the subject.

As would be understood by the skilled person, the threshold metric level of the classifier may refer to a control or reference population level. In one embodiment, a burst metric level may be classified as high or higher than normal if it is greater than a mean and/or median burst metric level of a reference population and a burst metric level may be classified as low or lower than normal if it is less than the mean and/or median burst metric level of the reference population. In this regard, a reference population may be a group of subjects who, for example, are of the same age, gender, ethnicity, disease status and/or prematurity as said subject for which the burst metric level is determined.

In particular embodiments, a higher level of the scaling exponent ($\alpha$) of the cumulative distribution function of all burst areas calculated indicates or correlates with a less favourable prognosis for a subject; and/or a lower level of the scaling exponent ($\alpha$) of the cumulative distribution function of all burst areas calculated indicates or correlates with a more favourable prognosis for a subject.

In particular embodiments, a lower level of the slope of the linear relationship between burst area and burst duration of individual bursts plotted in a double logarithmic fashion indicates or correlates with a less favourable prognosis for a subject, such as a preterm infant; and/or a higher level of the slope of the linear relationship between burst area and burst duration of individual bursts plotted in a double logarithmic fashion indicates or correlates with a more favourable prognosis for a subject, such as a preterm infant.

In other embodiments, a higher level of the slope of the linear relationship between burst area and burst duration of individual bursts plotted in a double logarithmic fashion indicates or correlates with a less favourable prognosis for a subject, such as a newborn infant with HIE; and/or a lower level of the slope of the linear relationship between burst area and burst duration of individual bursts plotted in a double logarithmic fashion indicates or correlates with a more favourable prognosis for a subject, such as a newborn infant with HIE.

In certain embodiments, a higher level of burst kurtosis indicates or correlates with a less favourable prognosis for a subject; and/or a lower level of burst kurtosis indicates or correlates with a more favourable prognosis for a subject.

In particular embodiments, a higher level of burst kurtosis indicates or is diagnostic of brain damage in a subject.

In certain embodiments, a higher level of burst skewness indicates or correlates with a less favourable prognosis for a subject; and/or a lower level of burst skewness indicates or correlates with a more favourable prognosis for a subject.

In particular embodiments, a higher level of burst skewness indicates or is diagnostic of brain damage in a subject.

The person skilled in the art would further understand that these prognostic and diagnostic burst metrics may not only be used in isolation for determining a prognosis and/or diagnosis in a subject, but more than one burst metric may be calculated for each subject and used in combination to compute a prognosis and/or diagnosis for that subject. Additionally, one or more of the diagnostic/prognostic burst metrics may be utilised in combination with one or more alternative diagnostic/prognostic metrics or markers, including other burst metrics, known in the art so as to determine a subject's prognosis and/or diagnosis.

In this regard, recent studies have shown that more conventional quantification of burst occurrence (Benders et al., 2014) and the presence of vigilance state cycling (a.k.a. sleep wake cycling; SWC) (Stevenson et al., 2014) may inform brain health. These methods recently became available with the validation of burst detectors (Palmu et al., 2010) and the development of cyclicity measures for preterm EEG monitoring (Stevenson et al., 2014). Accordingly, such methods may be used in combination with those described herein to determine a subjects prognosis and/or diagnosis.

So that preferred embodiments may be described in detail and put into practical effect, reference is made to the following non-limiting Examples.

Example 1

Example 1 demonstrates the use of EEG for acquiring the electrical activity of a subjects brain and burst metrics measured include mean burst duration and its coefficient of variability, the relationship between burst duration and burst size/area and the scaling exponent ($\alpha$) of the cumulative distribution function. In this Example, the invention is used to correlate the aforementioned burst metrics to the prognosis for neonates with hypoxic ischemic encephalopathy undergoing hypothermia treatment.

Subjects and Methods

The EEG recordings of twenty consecutively-admitted newborns (gestational age 39±2 weeks; see Table 1) that were monitored due to birth asphyxia at the tertiary level NICU of Helsinki University Central Hospital were analysed. The EEG was acquired from biparietal electrodes at 250 Hz using a NicOne or Olympic EEG device (Cardinal Healthcare and Natus, USA). Lengthy epochs of BS that were relatively artefact-free (120±90 minutes, range 30-600 minutes) were filtered at 1-20 Hz and further analysed with custom software in Matlab (Mathworks, Natick, Mass., USA). Clinical data collated from patient reports included: clinical reports from MRI scans acquired during the first week of life; birth details; NICU drug treatments; and outcome description in the patient reports at the last visit to routine neonatal outpatient clinic (age 12-39 months). Patients were divided into two categories based on their MRI findings (presence/absence of a thalamic lesion), and further into four categories based on their clinical outcomes (normal versus mildly, moderately, and severely abnormal; see Table 1). There was no statistical difference between the conceptional ages of the patient groups: thalamic lesion evident by MRI (38±2.4 wks), normal MRI (39.3±2.2 wks), poor outcome (38±2.6 wks) and normal outcome (39.6±2.2 wks). The use of patient data for this study was approved by the Ethics Committee of the Hospital for Children and Adolescents, Helsinki University Central Hospital.

Prior to the identification of bursts, the amplitude at each time point was determined using the well established method of the Hilbert transform, which is demonstrated for two individual bursts in FIG. 2. The instantaneous power or energy of EEG amplitude was subsequently calculated by taking the square of the amplitude at each time point. As shown in FIGS. 3 and 4, an adaptive thresholding method was then employed to detect the occurrence of bursts in the EEG. FIG. 5D provides a zoomed in image of a sample burst from FIG. 5B to illustrate the automated threshold and the burst measures, burst area/size (BA) and burst duration (BD) obtained therefrom. FIG. 5E-G demonstrates the three different metrics that were subsequently computed from the bursts occurring within each infant: i) mean burst duration (BD) and its coefficient of variability (CV) (FIG. 5G), ii) relationship between BD and size (i.e., burst area, BA) (FIG. 5F), and iii) scaling exponent ($\alpha$) of the cumulative distribution function (CDF) of the area of all bursts (FIG. 5E) in each recording. In addition, these novel measures were benchmarked against those established in prior research, namely the mean and CV of interburst interval (IBI) durations (Grigg-Damberger et al., Pediatric Neural, 1989). Notably, the novel metrics focus on the properties of bursts, specifically the heterogeneity of BAs, as well as the relationship between BAs and BDs. The slopes from the BA CDF plot and the BA vs. BD plot, such as those provided in FIGS. 4E and 4F respectively, of each infant were extracted as described herein.

Out of the twenty available neonatal datasets, four were excluded from further analyses due to the presence of excessive seizure activity (n=1), an early administration of sedative drugs that likely impacted on BS (n=1), or missing reliable clinical or MRI information (n=2). Group comparisons were carried out using a one way analysis of variance (ANOVA) followed by post-hoc analysis with a nonparametric Mann-Whitney U test. The correlations of clinical outcomes to burst metrics were calculated with Spearman correlation test.

Results

Figure 6:
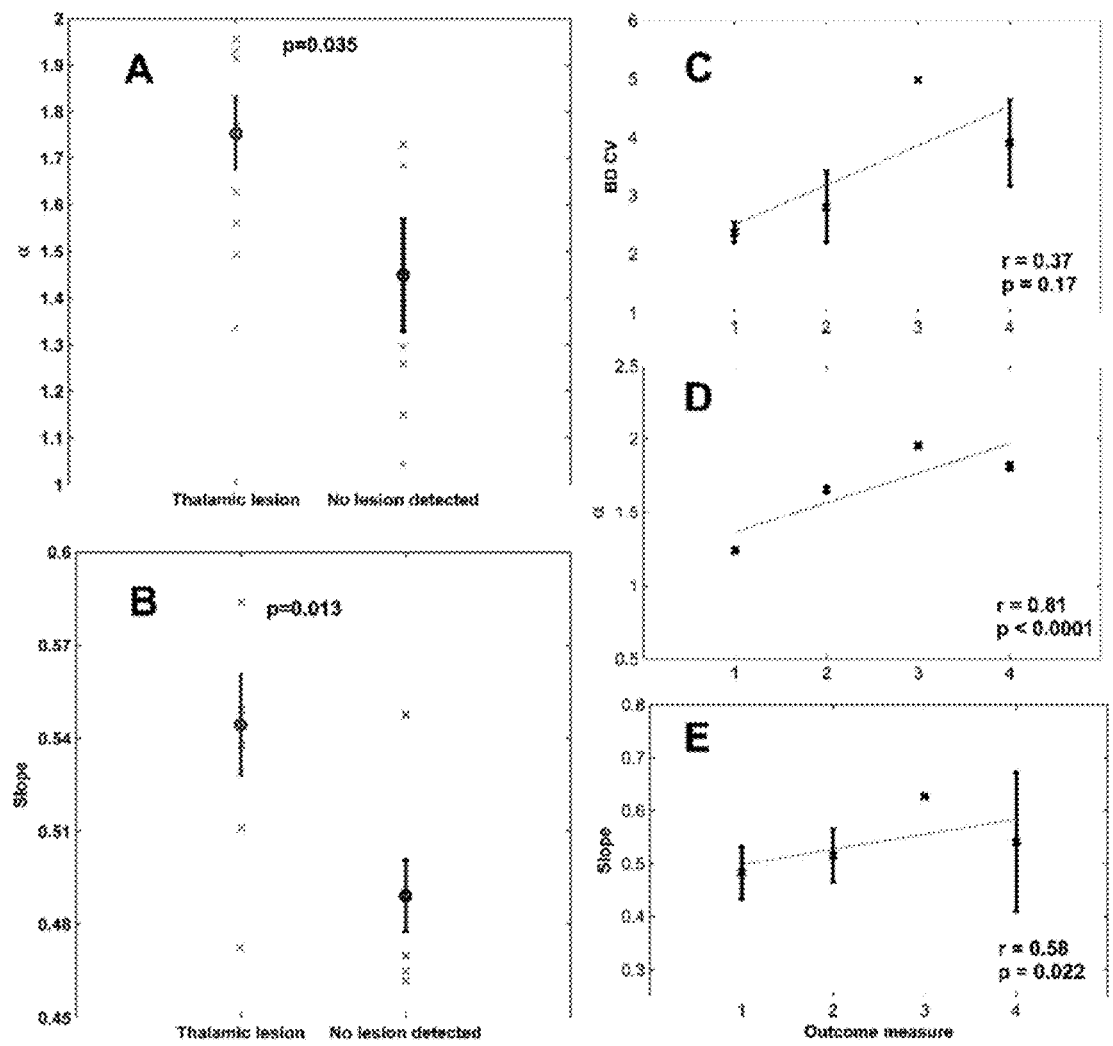
FIG. 6 demonstrates the suitability of the burst metrics as prognostic indicators in asphyxic infants.

FIG. 6A-B provides the comparison of the two prognostic burst metrics, scaling exponent ($\alpha$) of the CDF of BA and slope of the linear relationship between BA and BD respectively, from EEG readings during the first hours of life to MRI findings obtained several days later. These graphs show the mean±SEM, as well as individual data points.

FIG. 6C-E demonstrates the relationship of the three prognostic burst metrics, BD CV, scaling exponent ($\alpha$) of the CDF of BA and slope of the linear relationship between BA and BD respectively, from EEG readings during the first hours of life to clinical outcome categories later in infancy (1=normal; 2=mildly abnormal; 3=moderately abnormal; 4=severely abnormal). The analysis of the comparisons was performed using a one-way ANOVA as shown in each graph.

As is obvious from FIG. 4A-C, visual inspection of bursts occurring during post-asphyxic BS showed tremendous variety in their shape and form in both amplitude and power traces. In particular, the instantaneous power of an 80 minute EEG recording of FIG. 5C illustrates the self-similarity in shape and variability in size over time.

The variability of BA was thus examined by plotting its cumulative distribution function (CDF) and the relationship between BA and BD. As evidenced by FIG. 5E, the CDFs of BA show a robust, linear scaling relationship over several orders of magnitude when inspected in double logarithmic graphs. Such a distribution is known as scale free; i.e., it exhibits power-law scaling whose key behavior is captured by estimating the scaling exponent α (related to the CDF slope) (Clauset et al., SIAM Rev, 2009). A robust power law relationship between BA and BD over four orders of magnitude was also observed, as shown in FIG. 5F. Comparison of these burst metrics to subsequent MRI findings (FIG. 6A-B) showed that the scaling exponent was significantly higher ($F_{1, 16}=5.39$, $p=0.035$), as seen in FIG. 6A, and the slope between BAs versus BDs (on a log-log scale) was significantly steeper ($F_{1, 16}=7.89$, $p=0.013$), as seen in FIG. 6B, in babies with thalamic lesions. Moreover, FIGS. 6D-E demonstrate that both of these metrics also showed a significant correlation to neurodevelopmental outcome ($r=0.81$, $p<0.0001$, and $r=0.58$, $p=0.022$, respectively).

These findings were then benchmarked against more conventional statistical measures of burst intervals (BDs, BD CVs, and IBIs). Statistical analyses revealed that BD CV was significantly higher ($F_{1, 16}=4.92$, $p=0.042$) in babies with thalamic lesions compared to those with normal MRI findings. However, no difference was found in the mean duration of bursts ($F_{1, 16}=0.17$, $p=0.68$) or the mean IBIs ($F_{1, 16}=0.05$, $p=0.81$). In addition, BD CV showed a trend-level correlation to the developmental outcome ($r=0.37$, $p=0.17$), as shown in FIG. 6C. No correlation was seen between mean burst duration and any measure of IBIS.

Discussion

The findings show that novel burst metrics derived objectively from an EEG soon after perinatal asphyxia correlate significantly with later MRI findings and neurodevelopmental outcomes. These burst metrics—derived from the EEG using data-driven, user independent algorithms—correlate with the prospective clinical course of asphyxic newborns undergoing hypothermia treatment where traditional measures of IBIs or resolution of BS have little or no prognostic reliability (Thoresen et al., Pediatrics, 2010; Hallberg et al., Acta Paediatrica, 2010).

TABLE 1

| | EEG Dataset | | | Birth information | | | Clinical Outcome | | | |
| | | | | | | | | | Later | |
| Infant | Gender | Epoch Onset (hh:mm) | Duration of EEG epoch (mins) | Gestational age (weeks), weight (g) | pH at birth Apgar (1/5/10 min) | MRI info | Early outcome info | Later outcome (age/mos) | outcome age (years/ months) | Outcome class |
|---|---|---|---|---|---|---|---|---|---|---|
| 1 | m | 04:34 | 30 | 39 + 4 3780 | 7.07 1/4/5 | normal | — | mild abn in vision and fine motor skills | 3 y 2 m | 2 |
| 2 | m | 4:39 | 120 | 39 + 2 3390 | 6.95 1/1/5 | Excluded from main analysis due to lack of follow-up data | | | | |
| 3 | m | 15:54 | 120 | 34 + 5 2525 | 6.71 0/0/6 | bilateral thalamus lesion | myoclonic epilepsy, spastic hemiplegia | mild hemiplegia and epilepsy | 2 y | 3 |
| 4 | m | 3:07 | 100 | 40 + 1 3030 | 6.76 2/4/4 | Excluded from main analysis due to lack of follow-up data | | | | |
| 5 | m | 2:13 | 330 | 40 + 0 3830 | 7.02 2/3/5 | wide bilateral thalamus and basal ganglia lesion | infantile spasms, dystonic CP, mental retardation | severe CP | 2 y | 4 |
| 6 | m | 3:07 | 120 | 40 + 3 3960 | 6.93 1/4/5 | brain normal, mild subdural hematoma | mild abn in gross & fine motor skills, visual perception & speech, behavioural issues | normal | 2 y 9 m | 1 |
| 7 | m | 2:13 | 90 | 40 + 3 5778 | 7.10 0/0/1 | thalamic lesions | died | | | 4 |
| 8 | m | 5:56 | 120 | 41 + 4 3625 | 6.89 2/3/5 | normal MRI | normal at 1 y | normal | 2 y 2 m | 1 |
| 9 | f | 9:04 | 180 | 40 + 1 3190 | 6.86 1/1/1 | severe thalamus lesion | died | | | 4 |

TABLE 1-continued

| | | EEG Dataset | | Birth information | | Clinical Outcome | | | | |
|---|---|---|---|---|---|---|---|---|---|---|
| | | | | | pH at | | | | Later | |
| Infant | Gender | Epoch Onset (hh:mm) | Duration of EEG epoch (mins) | Gestational age (weeks), weight (g) | birth Apgar (1/5/10 min) | MRI info | Early outcome info | Later outcome (age/mos) | outcome age (years/ months) | Outcome class |
| 10 | f | 8:32 | 120 | 41 + 3 2688 | 6.80 2/2/5 | severe thalamus and cortical lesion | lost in follow-up (transfer to other hospital) | motor dysfunction, affects speech | 3 y 3 m | 2 |
| 11 | f | 16:05 | 160 | 36 + 4 3374 | 6.68 0/2/3 | wide thalamus and basal ganglia lesions | infantile spasms, dyskinetic CP | severe CP | 3 y 1 m | 4 |
| 12 | f | 04:59 | 40 | 41 + 1 3260 | 7.13 ap 9 | Excluded from main analysis due to lack of follow-up data | | | | |
| 13 | m | 5:16 | 100 | 42 + 0 4135 | 6.81 0/3/5 | normal | | normal | 2 y | 1 |
| 14 | f | | 90 | 41 + 5 4440 | pH not known 2/2/3 | Excluded from main analysis due to lack of follow-up data | | | | |
| 15 | m | 04:02 | 35 | 38 + 1 3300 | 6.84 1/4/5 | right th sign increase | normal at 11 m | normal | 1 y 5 m | 1 |
| 16 | m | 06:18 | 70 | 36 + 1 2430 | 7.30 1/4/5 | normal | | mild abnormality | 1 y 7 m | 1 |
| 17 | m | 4:16 | 60 | 41 + 0 3510 | 6.90 5/6/6 | normal | | normal | 13 m | 2 |
| 18 | m | 3:26 | 60 | 39 + 3 3550 | 7.15 1/1/1 | normal | | normal | 12 m | 1 |
| 19 | f | 2:57 | 70 | 39 + 5 3645 | 6.85 3/4/6 | normal | | normal | 12 m | 1 |
| 20 | m | 0:25 | 210 | 40 + 2 3520 | 6.87 0/0/1 | wide bilateral thalamus and basal ganglia lesion | died | | | 4 |

Example 2

Herein is described the fundamental statistical nature of endogenous brain events (hereafter called 'bursts') that constitute most of the early preterm EEG. Further, it is demonstrated in this Example that the preterm brain is governed by scale-free processes whose statistical information pre-dates clinical outcome. Indeed, characterizing scale-free behavior across gestational ages is shown to have value in predicting long-term outcome, highlighting the critical periods immediately after birth.

Materials and Methods
Data Collection

We analyzed EEG recordings of 43 preterm neonates (gestational age (GA) 22-28 weeks) that were monitored in the neonatal intensive care unit (NICU) at Lund University Hospital, Sweden. Other details of this cohort have been previously published (Wikström et al., 2012, Stevenson et al., 2014). Infants were included in the study after informed parental consent. The study was approved by the Regional Ethics Committee at Lund University.

The EEG was acquired at the biparietal P3-P4 derivation at a sampling rate of 256 Hz using a NicOne amplifier (Cardinal Healthcare, Madison, Wis., USA). We selected relatively artefact-free EEG epochs (90-120 minutes) at four postnatal ages: 12, 24, 48 and 72 hours. Each recording was exported to MATLAB (Mathworks, Natick, Mass., USA), bandpass filtered (0.2-20 Hz) and further analyzed with custom software.

All infants underwent standardized neurodevelopmental testing at 2 years corrected age with the Bayley scales of infant development, version II (BSID-II). The BSID-II provides developmental scores for cognition (Mental Development Index, MDI) and motor skills (Psychomotor Development Index, PDI). In addition, two dichotomous outcome groupings were used: First, infants were considered optimal vs suboptimal based on a cut-off MDI score of 85. This cut-off score is minus 1 standard deviation from a mean MDI of 100. Second, a composite classification (good vs poor) was created from observing one or more of the adverse outcomes (MDI<70, PDI<70, cerebral palsy, blindness, deafness, or death).

Extracting Features of Cortical Bursts in Preterm Infants

Figure 7:
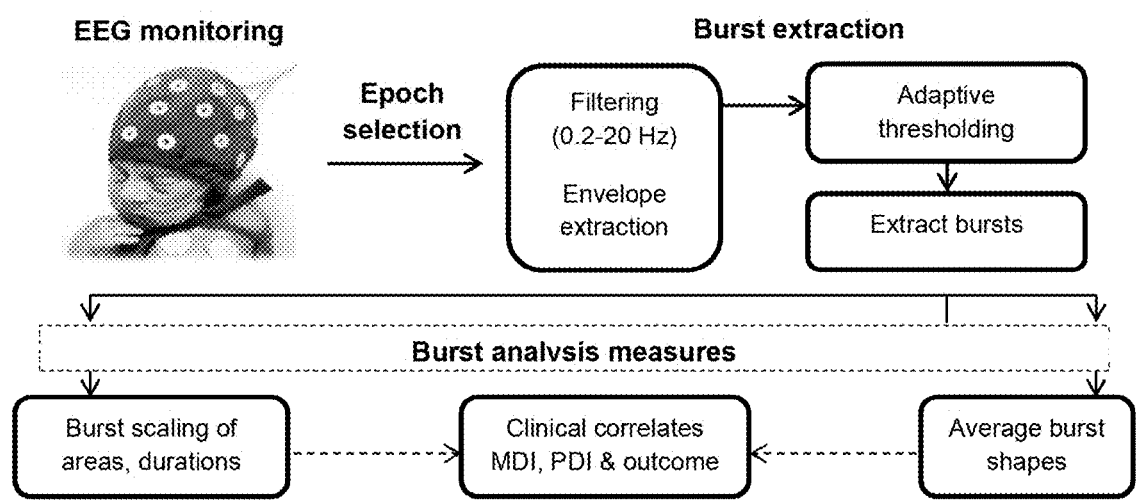
FIG. 7 demonstrates a schematic of cortical burst analysis procedure for preterm EEG recordings.

FIG. 7 illustrates the analysis procedure applied on 90-120 min EEG epochs selected from the long-term EEG monitoring data. Bursts were extracted and their statistical properties were characterized from each available recording. To understand the mechanisms of cortical burst generation, we employed methods used to examine burst shapes in physical systems (Sethna et al., 2001, Spasojevic et al., 1996; Baldassarri et al., 2003; Colaiori et al., 2004), recently adapted for newborn neurophysiological data to further elucidate scale-free bursting patterns in the preterm EEG (Roberts et al., 2014). Specifically, these methods quantify two aspects of burst morphology: First, the distribution of burst durations and burst areas are quantified across a wide spectrum of scales, providing insights into their putative scaling properties (see FIG. 8C). To study scaling relationships present between burst durations and burst areas, we also estimate their linear regression in log-log coordinates (see FIG. 8D), yielding a regression slope (S). Second, the average shape of bursts at different time-scales are estimated, which speaks to their underlying dynamical mechanisms (Papanikolaou et al., 2011, Roberts et al., 2014a). Average burst shapes are quantified by the change in symmetry ($\Sigma$) and sharpness (K) across burst durations from 200 ms up to 6 s in length.

These features of burst duration, area, and shape permit rapid, automated analyses of burst statistics from EEG epochs acquired at each postnatal age across gestational ages which we then correlate against clinical outcome indices. Statistical comparisons were conducted via general linear model fitting (GLM) and one-way analysis of variance (ANOVA). The GLM yields Pearson correlation coefficients (R) of burst statistics against continuous variables (i.e., GA in days; MDI and PDI scores between 50-120), and dichotomic outcome variables (0=good outcome, 1=poor outcome).

Results

Scale-Free Bursts Hours after Preterm Birth

Figure 8:
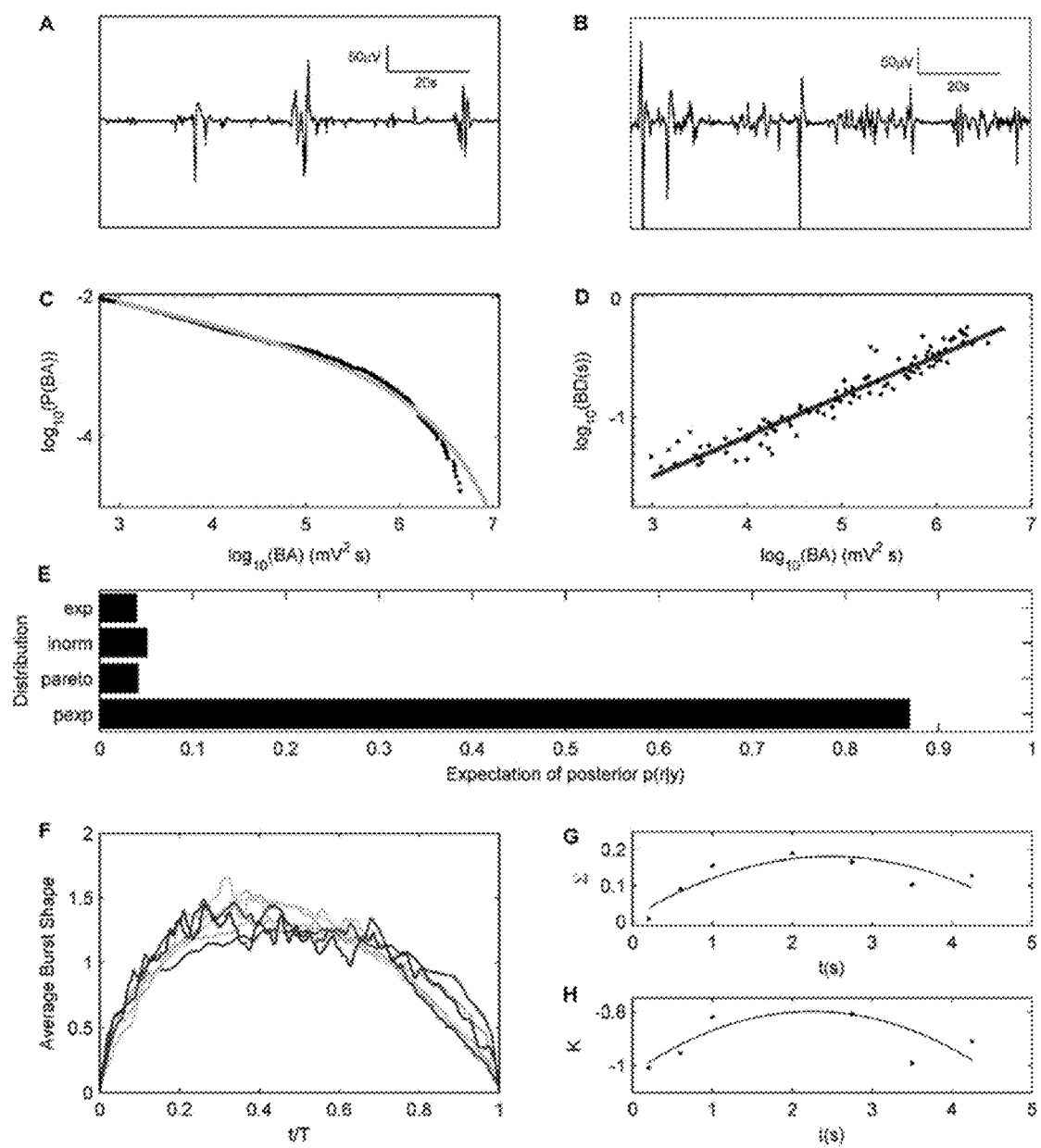
FIG. 8 demonstrates the results from preterm EEG analyses.

Visual inspection of bursts occurring in the EEG of these very preterm infants characteristically shows discontinuous, bursting EEG activity at 12 hours (FIG. 8A; discontinuous EEG activity with clear bursts and inter-burst periods) and 72 hours after birth (FIG. 8B; an increase in background EEG activity with smaller inter-burst periods). We first studied burst scaling as captured in the cumulative distributions (CDFs) of burst areas (FIG. 8C) and the relationship between burst area and burst duration (FIG. 8D). Burst areas and burst durations clearly reveal scale-free relationships present across nearly three orders of magnitude. At 12 hours, the CDF (FIG. 8C) is closely described by an exponentially truncated power law (shown in green), while the corresponding scaling relationship of burst areas with durations (FIG. 8D) exhibited a linear regime in double-logarithmic coordinates (shown in red).

To formally test the validity of scale-free behaviour in our data, we examined the empirical shapes of burst area CDFs against four theoretical distributions: power law (pareto), power law with exponential cutoff (pexp), log-normal (lnorm) and exponential (exp) (Clauset et al, 2009). We assessed the candidate fits for the data using log model evidence and Bayesian Model Selection (Stephan et al, 2009). This test indicates that the exponentially truncated power law is clearly the best description of the scaling process present in our data (FIG. 8E; the expectation of the posterior gives the probability that the model (r) explains observed data events (y)). We also examined the average burst shape at sequential timescales (FIG. 8F; 200 ms (red), 600 ms (yellow), 1 s (light green), 2 s (green), 2.75 s (cyan), 3.5 s (blue) and 4.25 (purple)), observing changes in burst symmetry (a measure of burst skewness, FIG. 8G), and sharpness (a measure of burst kurtosis FIG. 8H). Both of these measures show a concave-down relationship as a function of burst duration (FIGS. 8G-H; solid lines show best fitting quadratic).

In summary, these analyses assert the presence of power law scaling in the bursty cortical activity of the preterm as soon as 12 hours after birth. Whilst the bursts converge toward simple shapes, there is a subtle but systematic change in burst symmetry and sharpness as a function of time scale. For the subsequent analyses, we extract three robust burst metrics: (1) slope (S) of the linear relationship between burst areas and burst durations in log-log coordinates; (2) change in symmetry ($\Sigma$) of bursts across timescales and (3) corresponding change in sharpness (K) of bursts across timescales. These metrics together capture the heterogeneity of bursts, their shape, size, and overall temporal evolution over the first few days of preterm infant life.

Relationship of Burst Features to Gestational Age

Having established the presence of scale-free statistics, we next studied how the three markers of early cortical activity (scaling slope S; burst symmetry $\Sigma$; burst sharpness K) varied with gestational age (GA) in the very preterm infants. At 12 hours, S values significantly co-varied with GA ($R=0.22$, $p<0.02$, FIG. 9A), with lower slopes occurring in the most preterm infants (22-24 weeks) and higher slopes in babies of a higher GA (25-28 weeks). Values of S did not co-vary with GA at 24, 48 and 72 hours after birth. Mean sharpness (K) for bursts (>2 s duration) also significantly correlated with GA at 12 hours ($R=0.29$, $p=0.0071$, FIG. 9B), but there was no correlation at 24, 48 and 72 hours. Mean symmetry ($\Sigma$) for bursts (>2 s duration) did not correlate with GA at any postnatal epoch period between 12 to 72 hours. The burst metrics S and K were also highly correlated at 12 hours such that lower S generally corresponded with higher K ($R=0.41$, $p<0.0007$, FIG. 9C). This relationship was present at each postnatal period (24 hours $R=0.34$, $p<0.0003$; 48 hours $R=0.18$, $p<0.007$; 72 hours $R=0.32$, $p<0.003$).

At a postnatal age of 12 hours, average burst shapes showed a specific dependence on burst duration in the most immature infants (GA 22-24 weeks) (FIG. 9D) which was not present at later GA (25-28 weeks, FIG. 9E). In particular, the burst sharpness (K) at longer durations (>1 s duration) differs between these gestational ages. Further we find that K at mid-ranged burst durations significantly correlates with gestational age (FIG. 9F), specifically durations from 1 s-2 s ($p<0.017$), 2 s-2.75 s ($p<0.0015$) and 2.75 s to 3.5 s ($p<0.049$). Bursts shorter than 1 a and longer than 3.5 s do not show any significant dependence on GA. The measured features of bursts were hence specifically related to GA of the baby.

Burst Metrics Predictive of Long-Term Outcome

We next regressed these burst metrics against neurodevelopmental outcomes. In the human infant, this can be assessed by examining their correlations with long-term neurodevelopmental outcomes. Thus we examined the potential for 5, K and $\Sigma$ to predict three later outcomes at the age of 2 years: (1) the Mental Developmental Index (MDI), (2) the Psychomotor Index (PDI), and (3) composite outcome measures.

These analyses are presented in Table 2. Of note, slope (5) values were predictive of MDI ($R=024$, $p<0.035$) as soon as 12 hours after birth, and was also predictive of composite outcome measures ($R=0.19$, $p<0.035$) at 72 hours. Mean sharpness (K) values for bursts (>2 s duration) at 12 hours were predictive of composite outcome ($R=0.29$, $p<0.007$). At 72 hours, K (bursts with >2 s duration) was predictive of all three outcome measures: MDI ($R=0.18$, $p<0.04$), PDI ($R=025$, $p<0.01$) and composite outcome ($R=0.18$, $p<0.034$). In contrast, mean symmetry ($\Sigma$) of bursts (>2 s duration) was only predictive at 72 hours of MDI ($R=0.28$, $p<0.01$) and PDI ($R=0.19$, $p<0.04$).

Figure 9:
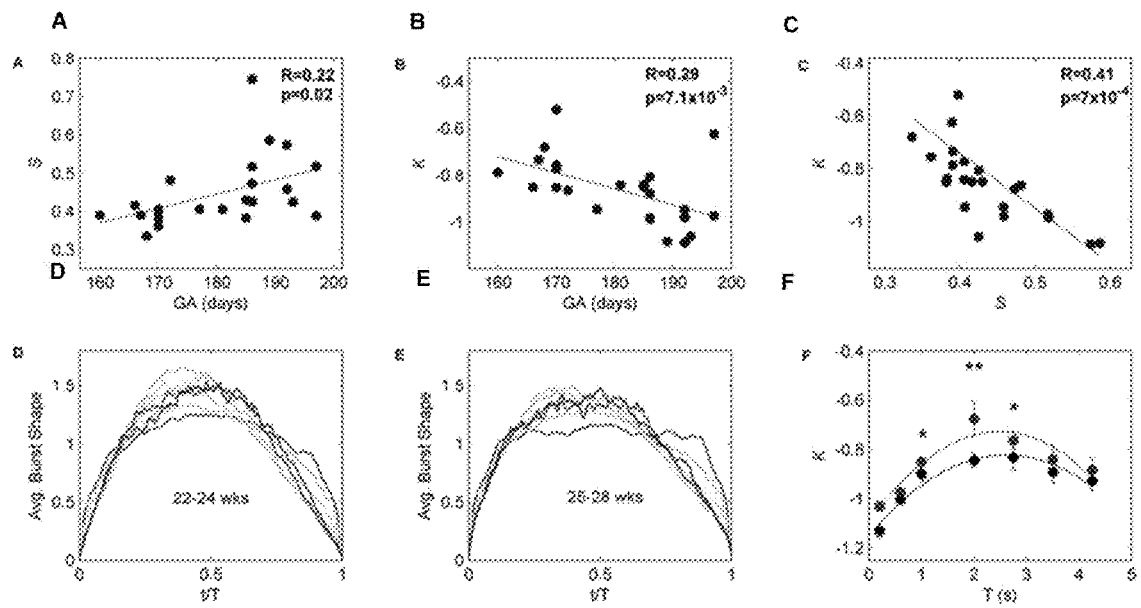
FIG. 9 demonstrates the relationship of burst metrics with gestational age 12 hours after birth.

Importantly, we find that both S and GA are correlated with MDI (Table 2). Further our burst metrics S and K are also correlated with GA (FIG. 9). In addition, we identified a weaker correlation of K with MDI at 12 hours (Table 2). This raises the possibility that the correlations of S and K with MDI arise only through the co-linearity of both variables with GA. Hence, we wanted to see whether our burst measures have independent predictive value over GA, which is already known in each given baby. This was done by assessing how GA affects the outcome prediction from burst measures. We employed statistical moderation (Baron and Kenny, 1986), to study via general linear models (GLM) whether GA strengthens the causal relationship between burst variables S and K to MDI.

$$MDI = b_0 + b_1 \cdot S + b_2 \cdot GA + b_3 \cdot S \cdot GA + \epsilon_1 \qquad 1)$$

$$MDI = b_{10} + b_{11} \cdot K + b_{12} \cdot GA + b_{13} \cdot K \cdot GA + \epsilon_{12} \qquad 2)$$

Figure 10:
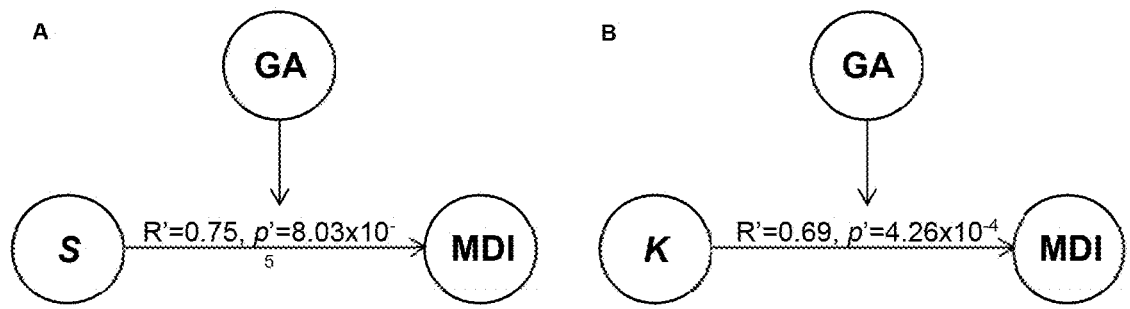
FIG. 10 demonstrates a path analysis diagram of correlations at 12 hours showing how gestational age moderates (A) slope to mental development index and (B) kurtosis to mental development index.

Thus, for GLM (1) (with regression coefficients $b_n$): $b_1$ (2514) and $b_2$ (6.7) quantify the contributions of S and GA, respectively, and $b_3$ (−13.33) quantifies the interaction between both S and GA, where $\epsilon_1$ (9.86) is the error term in the fit. This GLM (1) is highly significant in the case of S predicting MDI at 12 hours after birth (overall GLM (1): R'=0.75, p'=8.03×10$^{-5}$). In addition the value of $b_3$ is significant thus satisfying the condition for a moderating relationship (p<7.32×10$^{-4}$). Similarly, for GLM (2), $b_{11}$ (−1133.2) and $b_{12}$ (5.99) quantify the contributions of K and GA, respectively, and $b_{13}$ (5.94) is highly significant (p<0.02): thus K is also highly predictive of MDI (overall GLM (2): R'=0.69, p'=4.26×10$^{-4}$, $\epsilon_{12}$=11). Thus our metrics predict outcome even after taking into account the effect of GA, and the combined model yields a better predictor than either alone. Hence, formally, this relationship between S and MDI is moderated by GA. We represent these relationships using a simple path analysis diagram (FIG. 10).

Figure 11:
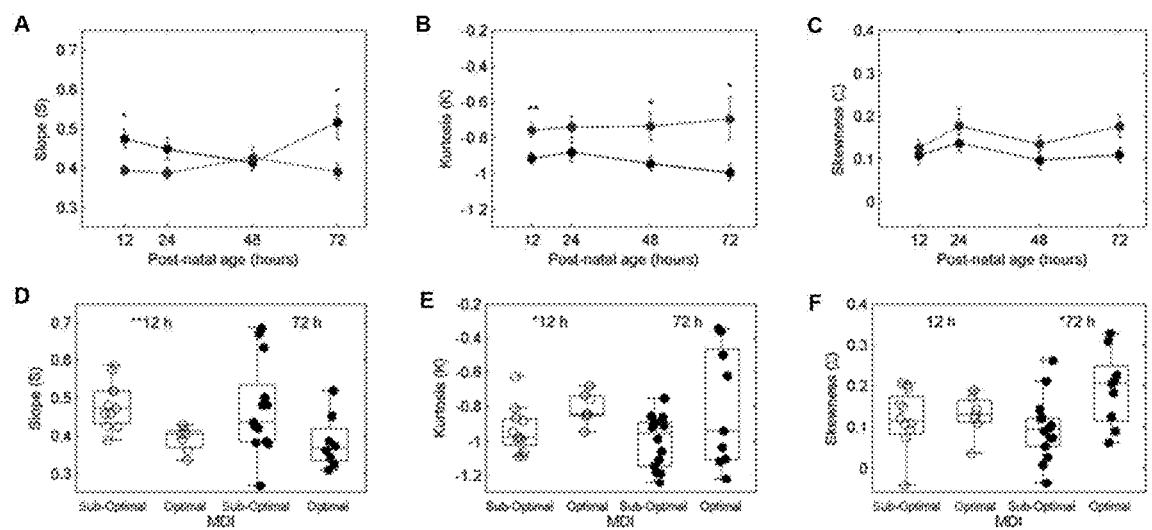
FIG. 11 demonstrates transitions of EEG burst metrics to clinical outcome over a 72 hour period.

The relationships between burst metrics and clinical outcome measures at each postnatal epoch period are summarized in FIG. 11 (Mean values±SEM bars representing good (black) versus poor (red) outcome for (A) Slope (S), (B) Kurtosis (K) and (C) Skewness (Σ); boxplots of sub-optimal (MDI<85) versus optimal (MDI>85) for (D) S values (E) K values and (F) Σ values for post-natal ages of 12 hours (transparent dots) and 72 hours (filled black dots); single asterisk represents p<0.05 and double asterisk represents p<0.01). Over a 72 hour period, burst metrics significantly co-vary with overall outcome (FIG. 11A-C) at some, but not at all postnatal ages. Further, a dichotomy of MDI into sub-optimal (MDI<85) and optimal outcomes (MDI>85), yields strong correlations at 12 hours for S (p<9×10−3) and K (p<0.03) values (FIG. 11D-F).

Discussion

We here establish that intermittent, spontaneous cortical bursts in the preterm brain exhibit classical scale-free properties, evidenced by a broad scaling regime of burst area in log-log coordinates. Moreover, these bursting dynamics appear to reflect important early neurodevelopmental processes as their characteristic statistics correlate with long-term neurodevelopmental outcome. The relationship between these burst metrics and outcome is moderated by gestational age. Our analysis hence identifies specific predictive properties of scale-free bursts in the preterm and their relationship to long-term neurodevelopment. We also highlight the crucial temporal transitions in these scaling statistics that occur already between 12 and 72 hours after birth. Scale-free processes arising from cortical activity in the preterm may provide further understanding of early brain activity at the developmental phase when the fundamental thalamo-cortical and cortico-cortical pathways are still growing.

Recent neuroanatomical work has shown that major thalamo-cortical and cortico-cortical pathways are in the early stages of development during the first weeks of early preterm life (Kostović and Judaš, 2010). Hence, the observed scale-free behavior of cortical activity arises in a brain network that is immaturely wired (early GA neonates) or where wiring is still undergoing intensive organization (later GA neonates). Weed, our findings showed that cortical bursting dynamics are different in infants prior to (GA<24 weeks) versus those after (GA>24 weeks) which aligns with the growth of first thalamo-cortical pathways (cf. Kostović and Judaš, 2010). Research using animal models shows that at early phases of cortical pathway development, these sparse connections give rise to intermittent spontaneous activity transients (SATs)—a characteristic feature of immature brain activity (Ben-Ari, 2001, Khazipov and Luhmann, 2006, Vanhatalo and Kaila, 2006, Blankenship and Feller, 2009, Hanganu-Opatz, 2010, Kilb et al., 2011, Colonnese and Khazipov, 2012). These events are thought to be the key functional driver of neuronal development where the deprivation of neurons leads to apoptotic cell death in experimental models (Kilb et al., 2011, Nimmervoll et al., 2013), while the overall level of bursting activity relates to prospective structural growth in the human preterm babies (Benders et al., 2014). Moreover, disruption of these events leads to disorganized thalamo-cortical connectivity and neuronal death (Catalano and Shatz, 1998, Milner et al., 2012). In this study, we demonstrate that features of cortical bursts in the early preterm do reflect immature cortical pathways which readily relate to neurodevelopmental consequences as indicated by our findings.

The presence of scale-free activity provides insight into system disturbances, potentially arising due to interplay between excitation and inhibition in cortical pathways and, more broadly, complex dynamics within neuronal networks, particularly in the face of scarce metabolic resources (Roberts et al., 2014a). Early developing neuronal circuits have been studied in detail at the cellular level (Blankenship and Feller, 2009, Hanganu-Opatz, 2010, Kilb et al., 2011) but little is quantitatively known about systems level brain dynamics in neonatal brains. It has been established in in vivo tissue slices that a shift in endogenous balance results in spontaneous cortical bursts exhibiting "neuronal avalanches", occurring when a system is bordering on the cusp between stability and instability (Beggs and Plenz, 2003). This avalanche-type behavior has been studied in a variety of neuronal recordings (Friedman at al., 2012, Meisel at al., 2012) highlighting that cortical activity may be generated via self-organized networks within the human cortex. In physical systems, self-organization further elucidates the unpredictable nature of a system at a critical state, resulting in fluctuations spanning a broad range of sizes (Sethna et al., 2001).

The recent observation of scale-free processes in hypoxic term infants with burst suppression (Roberts at al., 2014a) opens novel insights into critical states of cortical activity under the constraints of metabolic depletion. Using similar methods and more stringent statistical tests (i.e., Bayesian model selection), the present study establishes that scale invariant distributions exist in preterm EEG data—a characteristic feature recently identified as a key, but challenging objective (Fransson at al., 2013). Our results thus provide insight into a neurodevelopment window in the early preterm, where classical scale-free processes characterize potential system disturbances in cortical pathways hours after birth.

Transitions in Burst Dynamics at Early Gestational Ages

Previous analyses of preterm EEG have established the developmental trajectory of burst properties, with an increase in their duration and decrease in their amplitudes with GA (Vanhatalo at al., 2005, Tolonen at al., 2007, André at al., 2010). The intra-burst activities are also known to change with development (Tolonen at al., 2007, André at al., 2010), as well as after medication (Malk et al., 2014) or brain lesions (Okumura et al., 2002). These prior findings suggest that the burst shape analysis advanced in the present report may find diagnostic use in preterm babies, akin to recent evidence from full-term babies (Iyer at al., 2014, Roberts at al., 2014a). In our study of preterm neonates, bursting statistics change substantially over the 72 hour period after birth, either in response to treatment in the NICU, spontaneous metabolic recovery, or conversely due to progression of underlying neuronal disturbances. Further clarifying how these burst metrics reveal critical periods that predict outcome is to be the focus of future work.

Early Prediction of Long-Term Neurodevelopment

Early prediction of long-term neurodevelopmental outcome remains a major bedside challenge as very preterm infants that survive into early childhood have a high likelihood of developing mental disability or poor psychomotor performance at 2 years of age (Wood et al., 2000). The availability of outcome prediction within the first few days of life would allow early identification and provide the basis for improved guidance of intensive care interventions.

We observed significant relationships between statistical metrics of single channel EEG and later neurodevelopmental outcomes. Our results show that low slope values, moderated by the effect of gestational age, correlate with poor scores on the Mental Developmental Index (MDI, <85 on Bayley scales) or early death. We also show that higher burst sharpness (kurtosis), moderated by gestational age is indicative of poorer MDI. Importantly, our study quantifies the moderating role of gestational age on outcome. Thus, moderation was used to formally establish the effect of GA on our burst measures S and K. In the context of predicting likely neurocognitive outcome hours after preterm birth, this characterization of preterm EEG bursts is highly significant. Further we posit that these measures provide insight to the notion that system level disturbances (i.e., metabolic imbalance and poor synaptic connectivity) are acute reflections of the underlying neuronal circuitry in an immature cortex. It is also compatible with the interpretation that prenatal disturbances, such as placental infections or brain hemorrhages, predispose the child to adverse outcomes (Brown et al., 2013, Shapiro-Mendoza, 2014), and that our present EEG metrics capture the immediate consequences of these system-level disturbances coupled with the gestational age of the infant. In the absence of acute complications, the preterm infant is considered to be metabolically stable by the third day of life (Klein, 2002). We find that at 72 hours, skew and kurtosis values are predictive of mental and psychomotor outcome. This may indicate that temporal changes in bursting behavior reflect the impact of metabolic disturbances on neuronal integrity and recovery.

Most prior studies have focused on measuring overall amplitudes at a limited bandwidth (aEEG). As reviewed above, this approach requires trained reviewers and is vulnerable to artefacts. Despite these limitations, a relationship to later outcomes has been established (Olischar et al., 2004, Hellström-Westas and Rosen, 2005, Sisman et al., 2005, Wikström et al., 2012). These findings are compatible with the proposal that the total amount of brain activity is important for early brain health (see also (Benders et al., 2014)).

In summary, the analysis of bursts of electrical activity in neonatal EEG using the techniques of scale-free systems shows potential for predicting long-term outcome in preterm infants. Further, combining information from burst shapes with gestational age strongly predicts later outcome. Finally, we highlight the dynamic temporal changes in cortical bursting dynamics during the first early weeks of preterm development, as well as over the first days of postnatal life.

TABLE 2

Bivariate correlations (ANOVA) of burst metrics slope (S), skew ($\Sigma$) and kurtosis (K) as well as Gestational Age, and Mental Developmental Index (MDI), Physical Developmental Index (PDI) and Dichotomous Clinical Outcome.

| Metric | MDI | | PDI | | Overall Outcome | |
|---|---|---|---|---|---|---|
| | R | p | R | p | R | p |
| 12 hours | | | | | | |
| GA | 0.55 | $2 \times 10^{-4}$ | 0.06 | 0.29 | 0.32 | $3.8 \times 10^{-3}$ |
| S | 0.24 | 0.035 | 0.04 | 0.43 | 0.19 | 0.035 |
| $\Sigma$ | 0.01 | 0.98 | 0.00 | 0.89 | 0.01 | 0.62 |
| K | 0.17 | 0.08 | 0.10 | 0.192 | 0.29 | $7 \times 10^{-3}$ |
| 72 hours | | | | | | |
| GA | 0.41 | $1 \times 10^{-3}$ | 0.17 | 0.05 | 0.09 | 0.147 |
| S | 0.08 | 0.19 | 0.11 | 0.12 | 0.18 | 0.036 |
| $\Sigma$ | 0.28 | 0.01 | 0.19 | 0.04 | 0.14 | 0.067 |
| K | 0.18 | 0.04 | 0.25 | 0.01 | 0.18 | 0.034 |

Example 3

The hallmark of early EEG activity in very preterm infants is the presence of intermittently occurring bursts, or spontaneous activity transients (SAT), evident in the EEG trace as irregular high amplitude bursts of activity (Vanhatalo 2006, Andre et al., 2010). Hereinbefore described is a quantitative method to rapidly analyse EEG bursts to demonstrate that, after asphyxia in full-term infants, temporal changes in burst size and shape reveal abnormal electrocortical signatures impeding normal brain recovery (Roberts et al 2014) and predictive of long-term outcome (Iyer et al. 2014). These methods are fully automated and free from subjective qualitative assessments, thus enabling robust burst characterization, complementing conventional visually analyzed EEG measures such as the interburst interval (IBI) and burst counts (Wikstrom 2008, Hellstrom-Westas 2001). Herein, we demonstrate that quantitative measures of the early cortical bursts in the preterm EEG may acutely reflect, and even precede, the onset of IVH during the first days of life.

Materials and Methods

Data Collection and Analysis

We analysed EEG recordings of 25 preterm infants (gestational age 23-28 weeks; Table 3) that were monitored during their first three days of life in the Neonatal Intensive Care Unit (NICU) at Lund University Hospital, Sweden. The infants were part of a larger prospectively recruited cohort of very preterm infants from which qualitative and quantitative (IBI and measures of suppression) EEG analyses have been previously published (Wikstrom et al., 2012). Inclusion criteria for this analysis included age less than 28 weeks of gestation, availability of sufficiently artefact-free EEG epochs at postnatal hours 12 to 72, as well as clinically confirmed absence or presence of IVH via ultrasound at either day 1 or day 3 of life. EEG was acquired at the biparietal P3-P4 derivation at a sampling rate of 256 Hz using a NicOne amplifier (Cardinal Healthcare, Nicolet Biomedical, Madison, Wis. USA). Epochs of EEG (90-120 minutes) were selected at fixed post-natal time points of 12, 24, 48 and 72 hours from relatively artefact-free periods irrespective of vigilance state. Our quantitative EEG analysis focused on EEG epochs that preceded (pre-IVH) or followed (IVH) the confirmation of haemorrhage by ultrasound within the first three days of birth. The use of patient data for this study was approved by the Research Ethics Committee at Lund University.

Cranial ultrasound was performed routinely on day 1 (0-24 postnatal hours) and day 3 (48-72 postnatal hours) (Acuson XP 512, 7.5 MHz transducer, or Acuson Sequoia 8.5 MHz, Mountain View, Calif., USA). Data were analysed in three categories according to the severity of IVH: no IVH (grade 0); mild-moderate IVH (grades 1-2, i.e., germinal matrix hemorrhages or IVH without ventricular dilatation, respectively); and severe IVH (grades 3-4, i.e., IVH with ventricular dilatation or intraparenchymal involvement, respectively) (Papile, 1978). Contrasts on EEG analyses were then performed, comparing: i) infants with no IVH, ii) infants with IVH grades 1-2, and iii) IVH grades 3-4. We also analysed bursts from EEG epochs prior to finding the IVH by ultrasound to investigate whether burst shapes could indicate an impending or early onset phase of IVH. Thus, we compared each postnatal epoch with confirmed IVH with epochs temporally precedent to haemorrhage confirmation, referred hereafter as pre-IVH.

EEG data were exported to MATLAB (Mathworks, Natick, Mass., USA), band-pass filtered (0.2-20 Hz), and analysed using conventional and custom algorithms (Roberts et al., 2014). We first applied conventional analyses, namely interburst interval (IBI) and burst counts for the three preterm populations as classified in Table 3. We then used custom software to calculate changes in burst symmetry (skewness, $\Sigma$) and sharpness (kurtosis, K), across a wide range of burst durations (200 ms-6 s) (cf. Roberts et al., 2014). Statistical group comparisons of burst shape metrics were conducted using one-way analysis of variance (ANOVA).

Figure 12:
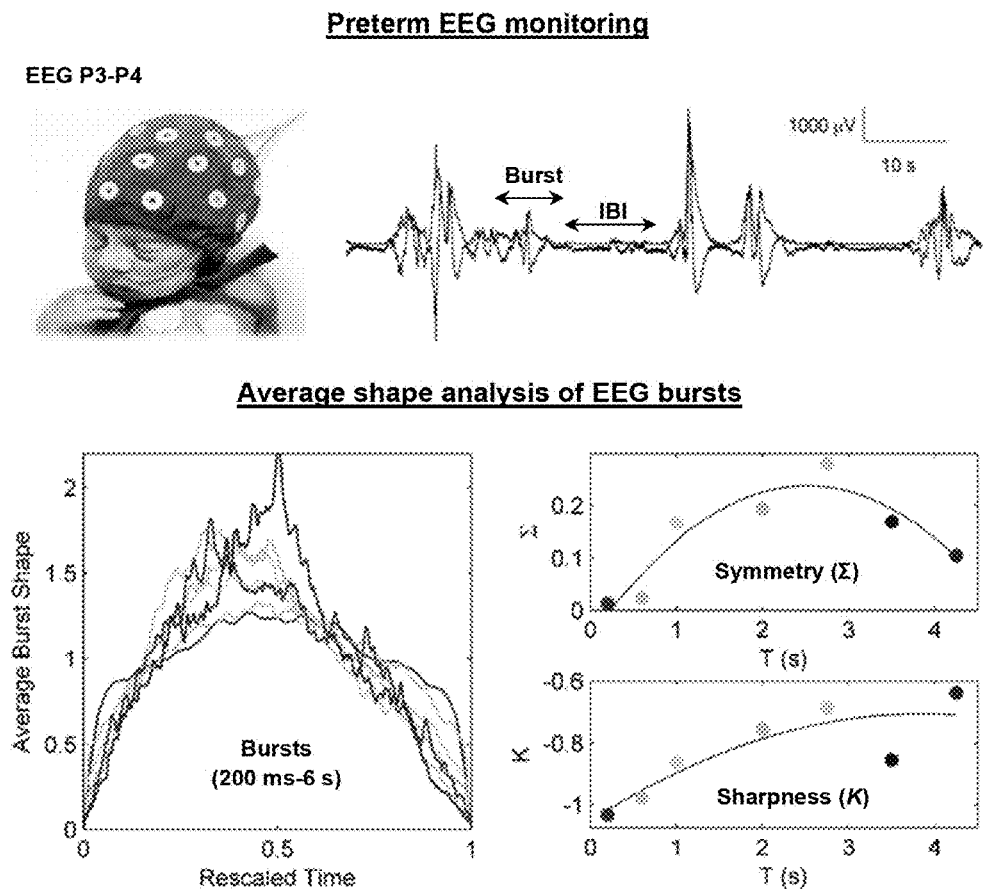
FIG. 12 demonstrates the analysis schema for each EEG recording epoch.

FIG. 12 shows a schematic for the analyses of each recording identified. In this regard, the biparietal P3-P4 signal is filtered before extracting bursts using an adaptive threshold technique on the signal envelope (blue overlay in EEG trace). Bursts area binned by duration (T) to seven groups and all bursts in a group are averaged, then scaled into unit time to analyse for their change in shape symmetry (skewness) and sharpness (kurtosis) across durations T. Durations in average burst shapes are colour coded to corresponding points in the skewness and kurtosis graphs: 200 ms (red), 600 ms (yellow), 1 s (light green), 2 s (cyan), 2.75 s (green), 3.5 s (purple) and greater than 4.25 s (blue). For each skewness and kurtosis graphs we fit a parabola across burst durations.

To assess diagnostic accuracy of burst shapes to identify IVH, we estimated true positive and false positive rates across a range of $\Sigma$ and K values, deriving corresponding receiver operating characteristic (ROC) curves. The ROC curves were further quantified by calculating the area under curve (AUC), a measure of diagnostic accuracy. We then summarized the clinical sensitivity and specificity of burst symmetry and sharpness values to discriminate between IVH and no IVH populations.

Results
Conventional Analyses

Figure 13:
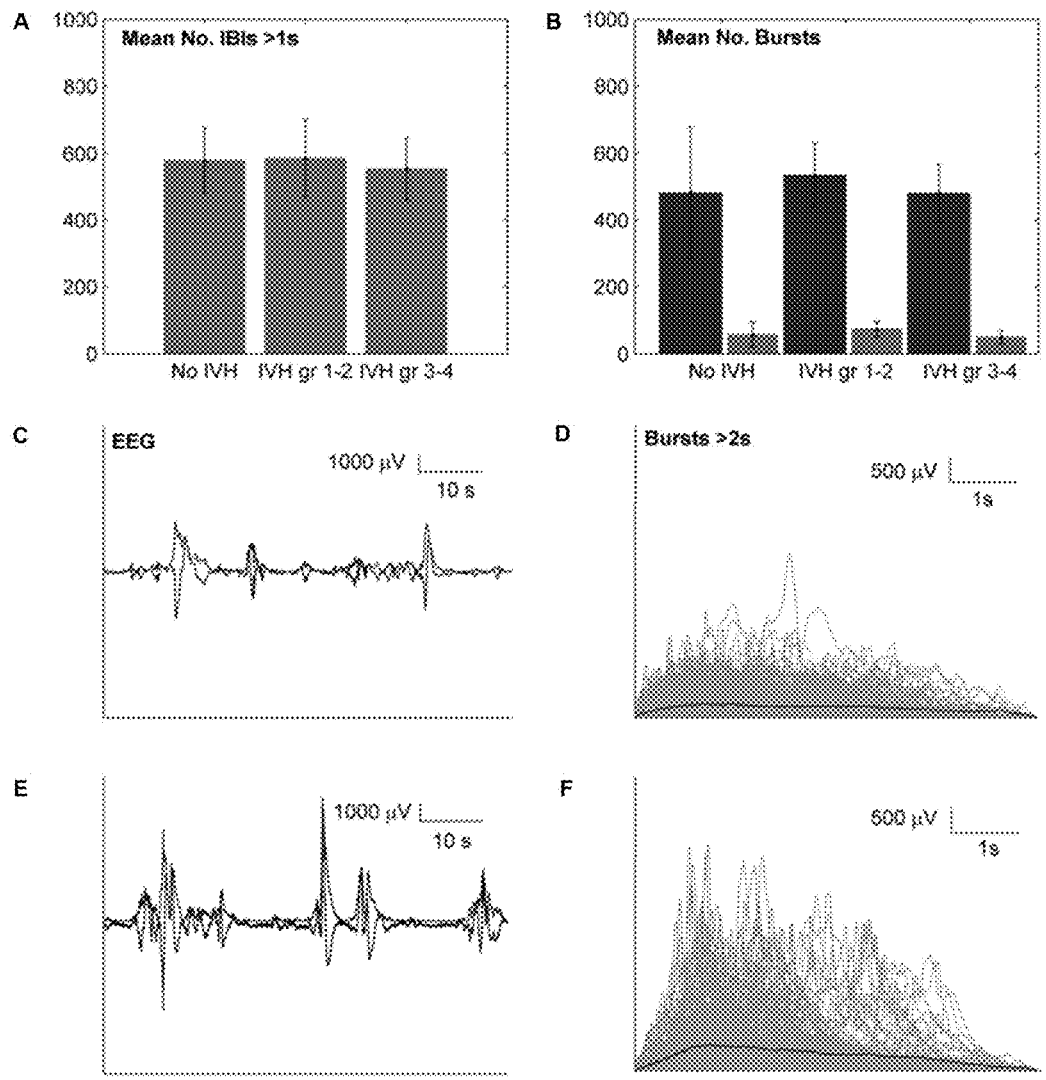
FIG. 13 demonstrates conventional analyses examining the bursting content of EEG epochs.

Conventional EEG measures did not differ significantly between the groups. Counts of IBIs with length >1 second were comparable in the babies with and without IVH (F=0.08, p=0.92). Further, burst counts comparing short bursts (F=0.43, p=0.65 for bursts <2 seconds) or long bursts (F=0.12, p=0.88 for bursts >2 s) did not show statistically significant differences (FIGS. 13A and B). Visual inspection of the preterm EEG showed characteristic bursts (SATs) in both groups, and no visually apparent difference in the overall activity between the groups (examples shown in FIGS. 13C and E). There were also no statistically significant differences in IBI or burst counts related to severity of IVH, gestational age, birth weight or 5-minute Apgar score.

A closer visual inspection of EEG traces of infants with IVH suggested that they might have higher amplitudes and greater burst areas than infants without IVH. These differences appeared more evident when we computed the instantaneous amplitude of the signals (see blue overlay traces in FIGS. 13C and E) and superimposed hundreds of bursts (FIGS. 13D and F). However, a closer inspection of conventional mean amplitudes (F=0.54, p=0.59) and mean areas (F=2.21, p=0.14) for bursts (>2 s duration) did not significantly differ between groups. Taken together, our findings suggest that the conventional measures (burst counts, IBIs, and amplitude changes) may not be able to distinguish EEG events in infants with IVH as compared to those with IVH.

Burst Shape Analyses

Figure 14:
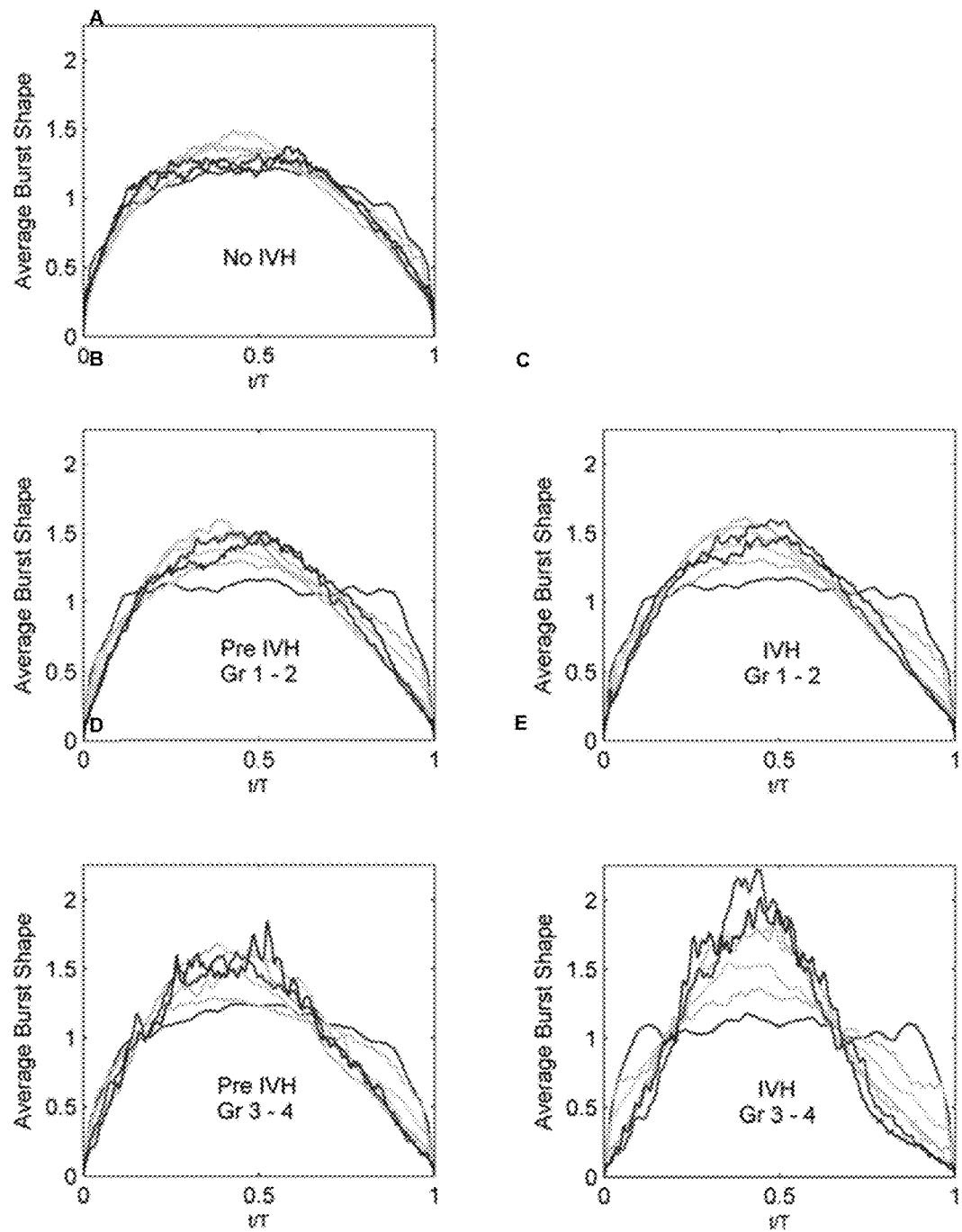
FIG. 14 demonstrates differences in average burst shape across increasing burst duration for infants with no IVH compared with pre-IVH and confirmed IVH, and FIG. 15 demonstrates visualization of the statistical differences in burst features for non-IVH and IVH populations (*$p<0.05$; **$p<0.01$).

We next examined the change in average burst shape as a function of burst duration using measures of burst symmetry ($\Sigma$) and sharpness (K). Visual comparison of grand average burst shapes across burst durations shows clear differences between the three IVH groups (FIG. 14). For each IVH grouping we calculated average burst shapes for pre-IVH grades 1-2 and 3-4 compared with NH grades 1-2 and 3-4, respectively (FIG. 14). Most notably, there was a strong increase in the sharpness of longer bursts (>2 s duration) with increasing severity of IVH. The longer bursts in infants with severe IVH (grades 3-4) were also asymmetric to the left, with sharper onset and slower decay compared to the bursts in infants with no or mild-moderate IVH (grades 1-2).

Statistical comparison of burst shapes between the three groups—no IVH, IVH 1-2, and NH 3-4—showed that bursts in the IVH infants were significantly sharper (higher K) at most burst durations (FIG. 14, (A) Grand average burst shape of all infants with no IVH, where short and long bursts have seemingly similar skewness and kurtosis. (B) Infants classified as mild-moderate undergo changes to average burst shape pre-IVH over the same burst duration hours before (C) presenting with grade 1 or 2 IVH. (D) The onset of more severe haemorrhage is significantly noticeable in grand average shape features in both pre-IVH infants and (E) during IVH), indicative of bursts in IVH infants having a characteristic temporal sharpness). For example, mean K values for bursts longer than 2 seconds differed significantly between IVH grades (F=13.78, p=8.3×10$^{-5}$). We also observed that asymmetry ($\Sigma$) of mid-duration bursts (1 s-3.5 s) differed significantly between infants with versus without IVH. The difference in longer bursts (>2 s duration) was statistically significant (F=6.91, p=0.014), indicating that infants with IVH tend to have more asymmetric bursts. No significant difference was seen in $\Sigma$ values between IVH severity grades (F=0.41, p=0.53).

Diagnostic Accuracy of Burst Shape Metrics

The overall accuracy estimated by area under the curve (AUC) was high in both groups (0.83-0.94). Importantly, sensitivity was fairly high (>0.8 and >0.6 for K and Σ, respectively) at all cutoff levels. A modest increase in sensitivity comes at a high price of substantial loss in specificity. We then tested systematically a range of K and Σ values for long bursts (>2 s duration), and found high sensitivity and specificity at selected cutoff levels for both pre-IVH and any IVH groups. Table 4 below summarizes the sensitivity and specificity values for a range of K and Σ cutoffs in this cohort.

Figure 15:
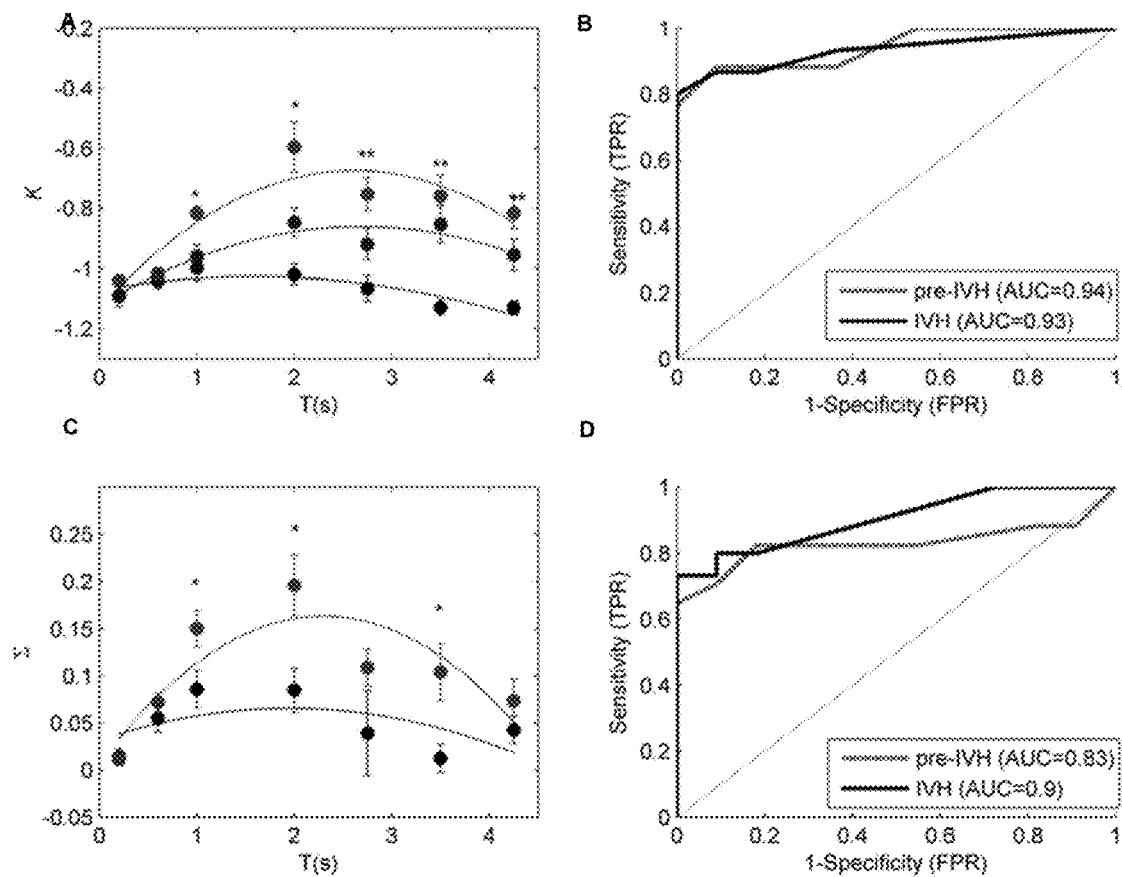

The potential of burst shape metrics to permit accurate identification of IVH was evaluated by use of receiver operating characteristics (ROC) for mean sharpness (K) (FIG. 15B), and symmetry (Σ) derived from longer bursts (>2 s duration) (FIG. 15D). We combined IVH 1-2 and IVH 3-4 (injury positive) and compared these infants to infants who did not develop IVH for each burst measure. Further, we performed the same analysis to pre-IVH infants by comparing them with no IVH infants.

Discussion

This study shows that two novel features of early cortical activity in very preterm infants—burst shape and asymmetry—are sensitive indicators of intraventricular haemorrhage. Cortical burst shapes can be rapidly and automatically analysed from continuously recorded EEG data and the presently used metrics are thus readily translatable into clinical settings. Our study also shows that these same metrics provide high diagnostic accuracy for identifying early IVH. Together, these findings hold promise for the everyday clinical challenge of real-time detection of impending IVH in very preterm babies.

Prior studies of EEG abnormalities in the presence of vascular lesions have focused on late EEG features, particularly the presence of positive rolandic sharp waves (PRS) (Clancy et al., 1984; Okumura et al., 1999). These PRS waves are identified as sharp, discrete transients of short duration (≤400 ms), which provide a relatively reliable sign of previously experienced IVH and white matter injury. The overall levels of early aEEG/EEG activity were recently shown to associate with early brain injury (Okumura et al., 2002; Olischar et al., 2007; Chalak et al., 2011; Hellstrom-Westas et al., 2001; Bowen et al., 2010). Our fully objective and patient-wise adaptive analysis method found no significant quantitative differences between study groups in IBI and burst count—the conventional measures used in studies of aEEG markers during acute IVH. However, overall burst shapes were significantly sharper and more asymmetric during the onset and occurrence of IVH as compared to infants without IVH. This suggests that the study of burst morphology in EEG may reflect disturbances in cortical activity prior to and during acute brain injury.

The observed changes in cortical burst shapes open a new window into developmental neurobiology. Recent advances in experimental animal models have established that the early preterm EEG bursts are cortical events, spontaneous activity transients (SATs), that play a crucial role in both neuronal survival and guidance of emerging network growth (Hanganu-Opatz et al., 2010; Colonnese at al., 2012). Studies in both animals (Colonnese et al., 2012) and humans (Omidvarnia et al., 2013) have shown that these events bind brain areas together, a necessary activity-dependent developmental mechanism for the developing brain connectome. It has also been demonstrated that the subplate layer in the developing cortex is responsible for orchestrating early cortical activity transients (Dupont et al., 2005). These mechanisms offer a potential developmental context to our finding—burst shapes were found to be most informative in the most severe, parenchymal brain lesions that extend to subplate or its vicinity (i.e., IVH grades 3-4). A change in the shape of scalp EEG bursts to sharper and leftward asymmetric forms could arise from a compromised subplate function, or from lesions in cortico-cortical tracts in the white matter, both of which may render cortical bursts more focal. Our recent theoretical work suggests, however, that changes in burst shapes may also arise from compromises in metabolic resources (Roberts et al., 2014), which is likely the case around IVH-related brain lesions as well.

Our present method offers support for common challenges in clinical applications of this kind in the neonatal intensive care environment. A particular technical advantage is that our method analyses extracted EEG events (bursts) without a need for continuous, uninterrupted streams of EEG signal. This allows automated selection of only good quality, artefact-free EEG epochs, without compromising analytical reliability. Hence, our burst-shape metrics will allow reliable diagnostics derived from EEG monitoring, even during NICU treatment where EEG records are frequently prone to disruption by clinical care artefacts, which are the most common compromise to all currently available analysis paradigms in EEG monitoring.

In conclusion, this study demonstrates that burst shape and burst asymmetry in the early EEG (as soon as 12 hours after birth) are indicators of IVH in very preterm infants. Early and accurate identification of abnormal burst shape and asymmetry may enable timely identification of infants with high risk for developing IVH, and may thus contribute to an increased understanding of pathophysiological mechanisms associated with IVH and future targeted neuro protective strategies.

TABLE 3

Clinical summary of the preterm population analyzed for this study.

|  |  | GA (weeks + days) | Birth Weight (g) | Apgar5 | cUS day 1 (0-24 h) | cUS day 2 (24-48 h) | cUS day 3 (0-48-72 h) |
|---|---|---|---|---|---|---|---|
| No IVH | 1 | 26 + 6 | 854 | 6 | 0 |  | 0 |
|  | 2 | 25 + 2 | 638 | 7 | 0 |  | 0 |
|  | 3 | 27 + 1 | 854 | 8 | 0 |  | 0 |
|  | 4 | 24 + 4 | 788 | 8 | 0 |  | 0 |
|  | 5 | 27 + 3 | 840 | 7 | 0 |  | 0 |
|  | 6 | 25 + 3 | 940 | 8 | 0 |  | 0 |
|  | 7 | 27 + 3 | 950 | 9 | 0 |  | 0 |
|  | 8 | 27 + 3 | 1148 | 8 | 0 |  | 0 |
|  | 9 | 25 + 1 | 732 | 9 | 0 |  | 0 |
|  | 10 | 25 + 5 | 946 | 5 | 0 |  | 0 |
|  | 11 | 25 + 5 | 780 | 8 | 0 |  | 0 |
| IVH (GR 1-2) | 12 | 24 + 2 | 730 | 6 | 0 |  | 1 |
|  | 13 | 24 + 2 | 646 | 5 | 2 |  | 2 |
|  | 14 | 26 + 4 | 951 | 8 | 1 |  | 1 |
|  | 15 | 25 | 725 | 6 | 0 |  | 2 |
|  | 16 | 27 | 970 | 7 | 1 |  | 2 |
|  | 17 | 23 + 5 | 584 | 9 | 0 |  | 2 |
|  | 18 | 27 + 4 | 1092 | 6 | — | 2 | 2 |
|  | 19 | 28 + 1 | 1230 | 7 | — | 2 | 2 |
|  | 20 | 27 + 4 | 630 | 6 | — | 2 | 2 |
| IVH (GR 3-4) | 21 | 22 + 6 | 580 | 7 | 0 |  | 3 |
|  | 22 | 26 + 4 | 670 | 3 | 4 |  | — |
|  | 23 | 24 + 3 | 796 | 6 | 0 |  | 3 |
|  | 24 | 27 | 950 | 7 | 0 | 3 | — |
|  | 25 | 24 + 2 | 730 | 6 | 3 |  | — |

Table legend: GA = gestational age, Apgar5 = Apgar score at 5 minutes, Gr-Grade. Ultrasound labels: cUS = Confirmed Ultrasound, 0 = no IVH, 1 = mild IVH, 2 = moderate IVH, 3 = severe IVH, 4 = very severe IVH, "—" = no examination, blank table entry = no ultrasound performed.

TABLE 4

Diagnostics for the sensitivity and specificity of K and Σ in predicting and identifying the IVH occurrence. A search through a range of thresholds yielded optimal values for K (−0.99) and Σ (0.13).

| | pre-IVH | | IVH | |
|---|---|---|---|---|
| Cutoff (K) | Sensitivity (%) | Specificity (%) | Sensitivity (%) | Specificity (%) |
| −0.98 | 76.5 | 100 | 80 | 100 |
| −0.99 | 88.2 | 90.9 | 86.7 | 90.9 |
| −1.00 | 88.2 | 81.8 | 86.7 | 81.8 |
| −1.06 | 88.2 | 63.6 | 93.3 | 63.6 |
| 0.16 | 64.7 | 100 | 73.3 | 100 |
| 0.14 | 70.6 | 90.9 | 73.3 | 90.9 |
| 0.13 | 82.4 | 81.8 | 80 | 90.9 |
| 0.12 | 82.4 | 45.5 | 80 | 81.8 |

The invention has now been described with reference to specific embodiments for the purposes of description to the person skilled in the relevant art. In particular, a number of novel methods for determining prognosis of a subject have been described herein. It should be understood, however, that the foregoing is not intended to be exhaustive or to limit the invention to a single disclosed embodiment. Rather, numerous alternatives, modifications and variations in light thereof will be apparent to those persons skilled in the art of the above teaching. Accordingly, the present invention is intended to embrace such alternative embodiments, whether discussed herein or apparent or relatively easily developed by the skilled artisan, as well as other embodiments that fall within the spirit and scope of the above described invention.

The invention claimed is:

1. A computer implemented method including the steps of:
    acquiring, with the one or more computing devices, a reading of electrical and/or electromagnetic activity from the brain of the subject over time;
    detecting, with the one or more computing devices, a plurality of bursts in said reading;
    determining, with the one or more computing devices, one or more burst metrics from said bursts wherein the one or more burst metrics are selected from the group consisting of: a scaling exponent of a cumulative distribution function of burst area of detected bursts, a slope of a linear relationship between burst area and burst duration of individual detected bursts plotted in a double logarithmic fashion, skewness of a waveform of the detected bursts and kurtosis of a waveform of the detected bursts;
    submitting, with the one or more computing devices, the one or more burst metrics to a classifier that determines a risk of developing brain damage and/or a detection of brain damage in the subject according to said metrics;
    obtaining the determined risk of developing brain damage and/or the detection of brain damage in the subject; and
    triggering an intensive care intervention to prevent or treat brain damage in response to the determined risk of developing brain damage and/or the detection of brain damage in the subject.

2. The computer implemented method of claim 1, wherein the subject has asphyxia or is at risk of developing asphyxia.

3. The computer implemented method of claim 1, wherein the subject is a newborn infant.

4. The computer implemented method of claim 3, wherein the newborn infant has hypoxic ischemic encephalopathy.

5. The computer implemented method of claim 1, wherein the classifier compares the one or more burst metrics to one or more threshold metric levels, such that an altered or modulated burst metric relative to the one or more threshold metric levels indicates or correlates with an increased or decreased probability of the subject having brain damage and/or having a poor prognosis.

6. The computer implemented method of claim 5, wherein the classifier comprises a database configured to compare the one or more burst metrics to the one or more threshold metric levels.

7. The computer implemented method of claim 5, wherein the one or more threshold metric levels are configured to determine the subject has or is at risk of developing intraventricular haemorrhage.

8. The computer implemented method claim 5, wherein the one or more threshold metric levels are or comprise a control or reference population level.

9. The computer implemented method of claim 1, wherein the reading of electrical and/or electromagnetic activity is an electroencephalogram (EEG).

10. An apparatus comprising:
    a detector for detecting a plurality of bursts from a reading of electrical and/or electromagnetic activity from the subject's brain;
    a processor coupled to memory, the processor programmed to:
        receive, the reading of electrical and/or electromagnetic activity from the subject's brain
        compute one or more burst metrics from the plurality of bursts, wherein the burst metrics are selected from the group consisting of: a scaling exponent of a cumulative distribution function of burst area of detected bursts, a slope of a linear relationship between burst area and burst duration of individual detected bursts plotted in a double logarithmic fashion, skewness of a waveform of the detected bursts and kurtosis of a waveform of the detected bursts;
        determine a risk of developing brain damage and/or a detection of brain damage in the subject by analysis of the one or more burst metrics with a classifier; and
        trigger an intensive care intervention to prevent or treat brain damage in response to the determined risk of developing brain damage and/or the detection of brain damage in the subject.

11. The apparatus of claim 10, further comprising a device for recording the reading of electrical and/or electromagnetic activity from the subject's brain.

* * * * *